United States Patent
Nakamura et al.

(10) Patent No.: US 9,115,341 B2
(45) Date of Patent: Aug. 25, 2015

(54) METHOD FOR EXPANDING HEMATOPOIETIC STEM CELLS USING HETEROCYCLIC COMPOUND

(75) Inventors: Takanori Nakamura, Minamisaitama-gun (JP); Atsushi Miyamura, Minamisaitama-gun (JP); Taito Nishino, Tokyo (JP); Norihisa Ishiwata, Minamisaitama-gun (JP); Katsuaki Miyaji, Funabashi (JP)

(73) Assignee: Nissan Chemical Industries, Ltd., Tokyo (JP)

( * ) Notice: Subject to any disclaimer, the term of this patent is extended or adjusted under 35 U.S.C. 154(b) by 900 days.

(21) Appl. No.: 12/746,507

(22) PCT Filed: Dec. 5, 2008

(86) PCT No.: PCT/JP2008/072190
§ 371 (c)(1), (2), (4) Date: Aug. 19, 2010

(87) PCT Pub. No.: WO2009/072626
PCT Pub. Date: Jun. 11, 2009

(65) Prior Publication Data
US 2010/0310537 A1    Dec. 9, 2010

(30) Foreign Application Priority Data
Dec. 5, 2007    (JP) .................. 2007-315168

(51) Int. Cl.
| | |
|---|---|
| C12N 5/00 | (2006.01) |
| C12N 5/0789 | (2010.01) |
| C07D 333/02 | (2006.01) |
| C07D 207/00 | (2006.01) |
| A61K 35/12 | (2015.01) |

(52) U.S. Cl.
CPC .............. *C12N 5/0647* (2013.01); *A61K 35/12* (2013.01); *C12N 2501/125* (2013.01); *C12N 2501/145* (2013.01); *C12N 2501/999* (2013.01)

(58) Field of Classification Search
None
See application file for complete search history.

(56) References Cited

U.S. PATENT DOCUMENTS

| | | |
|---|---|---|
| 7,351,841 B2 | 4/2008 | Owada et al. |
| 2003/0044978 A1 | 3/2003 | Young et al. |
| 2006/0069140 A1 | 3/2006 | Miyaji et al. |
| 2008/0027068 A1 | 1/2008 | Owada et al. |

FOREIGN PATENT DOCUMENTS

| | | |
|---|---|---|
| EP | 1 424 389 A1 | 6/2004 |
| JP | 2002-502599 A | 1/2002 |
| JP | 2002-502617 | 1/2002 |
| JP | 2006 506452 | 2/2006 |
| JP | 2006-61106 | 3/2006 |
| JP | 2006 527187 | 11/2006 |
| WO | WO 99/40783 | 8/1999 |
| WO | 2006 062240 | 6/2006 |
| WO | 2006 062247 | 6/2006 |
| WO | 2006 062249 | 6/2006 |
| WO | 2006 064957 | 6/2006 |
| WO | 2007 052808 | 5/2007 |
| WO | 2007 142308 | 12/2007 |
| WO | WO 2009/072624 A1 | 6/2009 |
| WO | WO 2009/072625 A1 | 6/2009 |

OTHER PUBLICATIONS

Aggarwal et al. 2012. Hematopoietic stem cells: transcriptional regulation, ex vivo expansion and clinical application. Curr Mol Med 12: 34-49; author manuscript available online at http://www.ncbi.nlm.nih.gov/pmc/articles/PMC3286491/pdf/nihms356893.pdf.*

Kanji S et al. 2011. Plasticity and maintenance of hematopoietic stem cells during development. Recent Pat Biotechnol. 5: 40-53; author manuscript available online at http://www.ncbi.nlm.nih.gov/pmc/articles/PMC3294454/pdf/nihms-356918.pdf.*

Nishino T et al. 2009. Ex vivo expansion of human hematopoietic stem cells by a small-molecule agonist of c-MPL. Exp Hematol 37: 1364-1377.*

Nishino T et al. 2012. New approaches to expand hematopoietic stem and progenitor cells. Expert Op Biol Therap 12: 743-756.*

(Continued)

*Primary Examiner* — Lora E Barnhart Driscoll
(74) *Attorney, Agent, or Firm* — Oblon, McClelland, Maier & Neustadt, L.L.P.

(57) ABSTRACT

An object of the present invention is to expand $CD34^+$ cells ex vivo efficiently in a short term using a biologically safe and inexpensively obtainable low molecular weight compound. A still another object of the present invention is to provide an expansion agent for $CD34^+$ cells useful for treatment of various hematopoietic disorders caused by dysfunctional hematopoietic stem cells and/or hematopoietic progenitor cells.

A method for expanding $CD34^+$ cells, which comprises culturing $CD34^+$ cells ex vivo in the presence of a compound represented by the formula (I) (wherein A, B, $L^1$, $L^2$, $L^3$, $L^4$, $R^1$, $R^2$, $R^3$, X and Y are defined in the description), a tautomer or pharmaceutically acceptable salt of the compound or a solvate thereof.

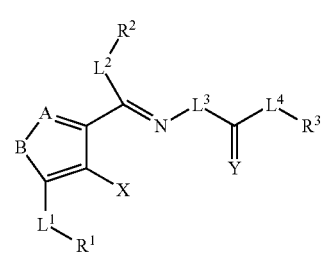

(I)

11 Claims, No Drawings

(56) References Cited

OTHER PUBLICATIONS

Li Lu, et al., "The Selective Enhancing Influence of Hemin and Products of Human Erythrocytes on Colony Formation by Human Multipotential ($CFU_{GEMM}$) and Erythroid ($BFU_E$) Progenitor Cells in Vitro", Exp. Hematol., vol. 11, No. 8, Sep. 1983, pp. 721-729.

Akihiko Taguchi, et al., "Administration of CD34+ Cells after Stroke enhances neurogenesis via angiogenesis in a mouse model", The Journal of Clinical Investigation, vol. 114, No. 3, Aug. 2004, pp. 330-338.

Donald Orlic, et al., "Bone marrow cells regenerate infarcted myocardium". Nature, vol. 410. Apr. 5, 2001, pp. 701-705.

Eriko Tateishi-Yuyama, et al., "Therapeutic angiogenesis for patients with limb ischaemia by autologous transplantation of bone-marrow cells: a pilot study and a randomised controlled trial", The Lancet, vol. 360, Aug. 10, 2002, pp. 427-435.

Joanne Kurtzberg, Md., et al., "Placental Blood as a Source of hematopoietic stem cells for transplantation into unrelated recipients", The New England Journal of Medicine, vol. 335, No. 3, 1996, pp. 157-166.

Hideo Ema, et al., "Colony Formation of Clone-Sorted Human Hematopoietic Progenitors" Blood, vol. 75, No. 10, May 15, 1990, pp. 1941-1946.

Lori Ishizawa, et al., "Immunomagnetic Separation of CD34+ Cells from Human Bone Marrow. Cord Blood, and Mobilized Peripheral Blood", Journal of Hematotherapy, vol. 2, 1993, pp. 333-338.

Aliza Cassel, et al., "Retroviral-mediated gene transfer into CD34-enriched human peripheral blood stem cells", Rapid Communication, Experimental Hematology, vol. 21, 1993, pp. 585-591.

Audrey C. Lam, et al., "Preclinical ex vivo expansion of cord blood hematopoietic stem and progenitor cells: duration of culture; the media, serum supplements, and growth factors used; and engraftment in NOD/SCID mice", Transfusion, vol. 41, Dec. 2001, pp. 1567-1576.

Kenneth Kaushansky, "Thrombopoietin and the Hematopoietic Stem Cell", Ann. N.Y. Acad. Sci., 1044, 2005, pp. 139-141.

Elen Rosler, et al., "Cocultivation of umbilical cord blood cells with endothelial cells leads to extensive amplification of competent $CD34^+ CD38^-$ cells", Experimental Hematology, 28, 2000. pp. 841-852.

Yasuhito Shimakura, et al., "Murine Stromal Cell Line HESS-5 Maintains Reconstituting Ability of Ex Vivo-Generated Hematopoietic Stem Cells from Human Bone Marrow and Cytokine-Mobilized Peripheral Blood", Stem Cells, 18, 2000, pp. 183-189.

John P. Chute, et al., "Inhibition of aldehyde dehydrogenase and retinoid signaling induces the expansion of human hematopoletic stem cells", Proc. Natl. Acad. Sci. USA., vol. 103, No. 31, Aug. 1, 2006, pp. 11707-11712.

Mohammed Milhem, et al., "Modification of hematopoietic stem cell fate by 5aza 2'deoxycytidine and trichostatin A", Blood. vol. 103, No. 11, Jun. 1, 2004. pp. 4102-4110.

Anskar Y. H. Leung, et al., All-trans retinoic acid (ATRA) enhances maintenance of primitive human hematopoietic progenitors and skews them towards myeloid differentiation in a stroma-noncontact culture system, Experimental Hematology, 33, 2005, pp. 422-427.

Liu, J. et al., " Ex Vivo Expansion of Enriched CD34+ Cells From Neonatal Blood in the Presence of thrombopoietin, A comparison With Cord Blood and Bone Marrow", Bone Marrow Transplant, vol. 24, pp. 247-252 (1999).

Nakamura, T. et al., "A Novel Nonpeptidyl Human C-Mpl Activator Stimulates Human Megakaryopoiesis and Thrombopoiesis", Blood, vol. 107, No. 11, pp. 4300-4307 (2006).

Cwirla, S. E. et al., "Peptide Agonist of the Thrombopoietin Receptor as Potent as the Natural Cytokine" Science, vol. 276, pp. 1696-1699 (1997).

Extended European Search Report issued Dec. 19, 2012 in Patent Application No. 08856980.1.

Office Action issued Oct. 15, 2013 in Japanese Patent Application No. 2009-544754 with English language translation.

* cited by examiner

METHOD FOR EXPANDING HEMATOPOIETIC STEM CELLS USING HETEROCYCLIC COMPOUND

CROSS-REFERENCE TO RELATED APPLICATIONS

This application is a National Stage of PCT/JP08/072190 filed Dec. 5, 2008 and claims the benefit of JP 2007-315168 filed Dec. 5, 2007.

TECHNICAL FIELD

The present invention relates to a method for expanding $CD34^+$ cells using a low molecular weight compound having a blood cell expanding effect, in particular, to a method for expanding $CD34^+$ cells in a culture medium containing various cytokines and/or growth factors in the presence of the compound and a material for cell therapy using the $CD34^+$ cells obtained by the expansion method.

BACKGROUND ART

Blood contains various lineages of blood cells having biological functions, such as the erythrocytic lineage associated with oxygen delivery, the megakaryocyte lineage generating thrombocytes, the granulocytic lineage associated with prevention of infections, the myeloid lineage such as monocytes and/or macrophages and the lymphocytic lineage responsible for immunity such as T cells and B cells. All these blood cells differentiate and mature from the common origin, hematopoietic stem cells, and are maintained and generated in an individual throughout its life. Hematopoietic stem cells are defined as cells having both pluripotency which allows them to differentiate into functional cells such as lymphocytes, erythrocytes and leukocytes and the ability to regenerate themselves while maintaining the pluripotency (self-renewal).

Previous studies have revealed that hematopoietic stem cells first diverge two ways into the myeloid lineage and the lymphoid lineage, then differentiate into myeloid stem cells (mixed colony forming cells, CFU-GEMM) and into lymphoid stem cells, respectively. Further, myeloid stem cells differentiate into erythrocytes via erythroid burst forming cells (BFU-E) and erythroid colony forming cells (CFU-E), into thrombocytes via megakaryocyte colony forming cells (CFU-MEG), into monocytes, neutrophils and basophils via granulocyte-macrophage colony forming cells (CFU-GM), and into eosinophils via eosinophil colony forming cells (CFU-EO), while lymphoid stem cells differentiate into T cells via T lymphoid progenitor cells and into B cells via B lymphoid progenitor cells. These myeloid stem cells and various hematopoietic progenitor cells derived from them are identified by the properties of colonies they form on soft agar, semisolid methylcellulose media or the like in the presence of various cytokines (Non-Patent Document 1).

In recent years, as a curative therapy for a number of intractable diseases such as various blood diseases attributed to hematopoietic dysfunction and immune dysfunction, cancer, immunodeficiency, autoimmune diseases and inborn error of metabolism, autologous or allogeneic transplantation of hematopoietic stem cells have been carried out. Quite recently, the effectiveness of hematopoietic stem cell transplantation in treating cerebral infarction, myocardial infarction and obstructive arteriosclerosis was reported (Non-Patent Documents 2, 3 and 4). Among them, bone marrow transplantation has been used in many cases of treatment and most established as a standard hematopoietic cell transplantation therapy. However, because for bone marrow transplantation, the human leukocyte antigens (HLA) of the bone marrow donor and the transplant recipient have to match closely, there is a problem that bone marrow from donors are in short supply. Besides, the need for at least 4 days of hospitalization and pain, fever and bleeding caused by collection of a large amount of bone marrow are a heavy burden to donors.

In addition to bone marrow, peripheral blood is also used as an alternative source of hematopoietic stem cells nowadays. Hematopoietic stem cells mobilized from the bone marrow to peripheral blood by administration of granulocyte colony stimulating factor (G-CSF) to a human are used for transplantation after enrichment using a blood cell separator. However, donors for peripheral blood hematopoietic stem cell transplantation have to bear a heavy burden of the need for administration of G-CSF for 4 to 6 consecutive days which may cause side effects (such as blood coagulation and spleen hypertrophy). Besides, because the efficiency of the mobilization of hematopoietic stem cells from the bone marrow to peripheral blood by G-CSF varies from donor to donor, hematopoietic stem cells are not obtained sufficiently in some cases.

Just recently, it was found that cord blood contains as many hematopoietic stem cells as bone marrow and is useful for hematopoietic stem cell transplantation (Non-Patent Document 5). Because cord blood transplantation does not require complete HLA matching and is less likely to cause severe acute graft-versus-host disease (GVHD) than bone marrow and peripheral blood transplantation, cord blood is established as useful and has been used more frequently. However, because cord blood is obtained in a small amount from one donor and does not contain many hematopoietic stem cells, its use is mainly limited to children.

To solve the above-mentioned problems with therapeutic hematopoietic stem cell transplantation, a technique for expanding hematopoietic stem cells and hematopoietic progenitor cells ex vivo is demanded, and various culture methods have been attempted so far.

Here, hematopoietic stem cells and hematopoietic progenitor cells, which are to be cultured, are explained. It was revealed that in human, hematopoietic stem cells and various hematopoietic progenitor cells derived from them are found in populations of $CD34^+$ cells expressing the CD34 molecule as a cell surface antigen, and hence hematopoietic stem cells can be enriched as a $CD34^+$ cell population (Non-Patent Document 6). Specifically speaking, they are often enriched by mixing a cell population to be separated with a CD34 antibody labeled with magnetic beads and magnetically collecting $CD34^+$ cells (Non-Patent Documents 7 and 8).

Conventional techniques for expanding hematopoietic stem cells and/or hematopoietic progenitor cells will also be explained. As mentioned above, since hematopoietic stem cells are more enriched in $CD34^+$ cells, $CD34^+$ cells are mainly used as the starting cells for expansion. Expansion of $CD34^+$ cells from $CD34^+$ cells in culture in the presence of a cytokine or a growth factor such as stem cell factor (SCF), interleukin 3 (IL-3), interleukin 6 (IL-6), interleukin 6 (IL-6)/soluble IL-6 receptor complex, interleukin 11 (IL-11), granulocyte colony stimulating factor (G-CSF), granulocyte-macrophage colony stimulating factor (GM-CSF), flk2/flt3 ligand (FL), thrombopoietin (TPO) and erythropoietin or Notch ligand (such as Delta 1) has been reported (Non-Patent Document 9). Among them, TPO is especially excellent in hematopoietic stem cell expansion effect and used for in most of cases of expansion (Non-Patent Document 10). Hematopoietic stem cells and hematopoietic progenitor cells expand in culture in the presence of such various cytokines and growth factors, but these cytokines and growth factors are all produced as recombinant proteins, it may be difficult to obtain them for expansion stably in a large amount at low cost quickly.

For ex vivo expansion of hematopoietic stem cells, coculture systems using a different type of cells as feeder cells in the presence of various cytokines were reported. For example, expansion of CD34+ cells in coculture with human bone marrow stromal cells was attempted (Non-Patent Document 11 and Patent Document 1). An attempt to expand CD34+ cells in the presence of TPO, FL and SCF using mouse bone marrow cell line HESS-5 was also reported (Non-Patent Document 12). However, these coculture systems use foreign cells, there is a risk that cells infected with an unknown pathogen whose existence has not been confirmed may also be transplanted to patients. Furthermore, when stromal cells from a different kind of animal are used, the stromal cells have to be separated completely from CD34+ cells because otherwise there is a risk of causing immune response in the recipient after transplantation.

In addition, ex vivo expansion of hematopoietic stem cells in culture in the presence of various cytokines combined with low molecular weight compounds, not just various cytokines only, has been reported. Examples of such low molecular weight compounds include copper chelators, the combination of a histone deacetylase inhibitor and a DNA methylase inhibitor, all-trans retinoic acid, aldehyde dehydrogenase inhibitors (Non-Patent Documents 13, 14 and 15 and Patent Document 2). However, addition of any of them is not effective enough since hematopoietic stem cells have to be cultured for about 3 weeks.

Patent Document 1: JP-A-2006-61106
Patent Document 2: JP-A-2002-502617
Non-Patent Document 1: Lu, L. et al.; Exp. Hematol., 11, 721-9, 1983
Non-Patent Document 2: Taguchi, A et al.; J Clin Invest., 114, 330-8. 2004
Non-Patent Document 3: Orlic, D et al.; Nature, 410, 701-5. 2001
Non-Patent Document 4: Tateishi-Yuyama, E et al.; Lancet, 360, 427-35. 2002
Non-Patent Document 5: Kurtzbert, J. et al.; New Eng. J. Med., 335, 157-66, 1996
Non-Patent Document 6: Ema, H. et al.; Blood, 75, 1941-6, 1990
Non-Patent Document 7: Ishizawa, L. et al.; J Hematother., 2, 333-8, 1993
Non-Patent Document 8: Cassel, A. et al.; Exp. Hematol., 21, 585-91, 1993
Non-Patent Document 9: Lam A C et al. Transfusion. 2001 December; 41 (12): 1567-76
Non-Patent Document 10: Kaushansky, K et al.; Ann NY Acad Sci., 1044, 139-141, 2005
Non-Patent Document 11: Rosier, E, et al.; Exp Hematol., 28, 841-52, 2000
Non-Patent Document 12: Shimakura, Y. et al.; Stem Cells, 18, 183-9, 2000
Non-Patent Document 13: Chute, J P et al.; Proc Natl Acad Sci USA., 103, 11707-12, 2006
Non-Patent Document 14: Milhem, M et al.; Blood., 103, 4102-10, 2004
Non-Patent Document 15: Leung, A Y et al.; Exp Hematol., 33, 422-7, 2005

DISCLOSURE OF THE INVENTION

Object to be Accomplished by the Invention

An object of the present invention is to expand CD34+ cells ex vivo efficiently in a short term using a biologically safe and inexpensively obtainable low molecular weight compound. A still another object of the present invention is to provide an expansion agent for CD34+ cells useful for treatment of various hematopoietic disorders caused by dysfunctional hematopoietic stem cells and/or hematopoietic progenitor cells.

Means to Accomplish the Object

The present inventors conducted extensive search for compounds having expansion activity to find a method for expanding CD34+ cells ex vivo. As a result, they found that the compounds represented by the following formula show excellent expansion activity on CD34+ cells, even in the absence of TPO and are highly useful as an expansion agent for cell populations rich in human hematopoietic stem cells and/or hematopoietic progenitor cells and accomplished the present invention.

Namely, the present invention relates:
(1) A method for expanding CD34+ cells, which comprises culturing CD34+ cells ex vivo in the presence of a compound represented by the formula (I), a tautomer, prodrug or pharmaceutically acceptable salt of the compound or a solvate thereof:

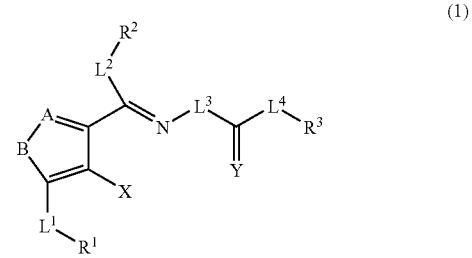

(1)

wherein A is a nitrogen atom or $CR^4$ (wherein $R^4$ is a hydrogen atom, a hydroxyl group (the hydroxyl group may be substituted with a $C_{2-6}$ alkenyl group or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), or $R^6$ and $R^7$ mean, together with each other, $-(CH_2)_{m1}\text{-E-}(CH_2)_{m2}-$ (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group, a $C_{2-14}$ aryl group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), B is an oxygen atom, a sulfur atom or $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)) (provided that when A is a nitrogen atom, B is not NH), $R^1$ is a $C_{2-14}$ aryl group (the $C_{2-14}$ aryl group may be substituted with one or more substituents selected from the group consisting of: a halogen atom, a carboxyl group, a nitro group, OCHO, a cyano group, a hydroxyl group, a protected hydroxyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group, a $C_{1-10}$ alkylcarbonyloxy group, a $C_{1-10}$ alkoxycarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyl group, the $C_{1-10}$ alkylcarbonyloxy group and the $C_{1-10}$ alkoxycarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a thiol group and an amino group (the thiol group and the amino group may be optionally substituted with one or more substituents selected from the group consisting of: a formyl group, a $C_{1-10}$ alkyl group, a $C_{2-6}$ alkenyl group, a $C_{2-6}$ alkynyl group and a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or two substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)))), $L^1$ is a bond, $CR^{10}R^{11}$ (wherein each of $R^{10}$ and $R^{11}$ is independently a hydrogen atom or a $C_{1-6}$ alkyl group (the $C_{1-6}$ alkyl group may be substituted with one or more halogen atoms)), an oxygen atom, a sulfur atom or $NR^{12}$ (wherein $R^{12}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), X is $OR^{13}$, $SR^{13}$ or $NR^{14}R^{15}$ (wherein $R^{13}$ is a hydrogen atom, a $C_{1-10}$ alkyl group, a $C_{2-6}$ alkenyl group, a $C_{2-6}$ alkynyl group or a $C_{1-10}$ alkylcarbonyl group (the $C_{1-10}$ alkyl group, the $C_{2-6}$ alkenyl group, the $C_{2-6}$ alkynyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), and each of $R^{14}$ and $R^{15}$ is independently a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), $R^2$ is a hydrogen atom, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkoxycarbonyl group, a $C_{1-10}$ alkylcarbonyloxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkoxycarbonyl group, the $C_{1-10}$ alkylcarbonyloxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), $L^2$ is a bond, $CR^{34}R^{35}$ (wherein each of $R^{34}$ and $R^{35}$ is independently a hydrogen atom or a $C_{1-6}$ alkyl group (the $C_{1-6}$ alkyl group may be substituted with one or more halogen atoms)), an oxygen atom, a sulfur atom or $NR^{16}$ (wherein $R^{16}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), $L^3$ is a bond, $CR^{17}R^{18}$ (wherein each of $R^{17}$ and $R^{18}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), an oxygen atom, a sulfur atom or $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), $L^4$ is a bond, $CR^{20}R^{21}$ (wherein each of $R^{20}$ and $R^{21}$ is independently a hydrogen atom, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), an oxygen atom, a sulfur atom or $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), Y is an oxygen atom, a sulfur atom or $NR^{23}$ (wherein $R^{23}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and $R^3$ is a $C_{2-14}$ aryl group (the $C_{2-14}$ aryl group may be substituted with one or more substituents independently represented by $—W^1(CW^2W^3)_m W^4$ (wherein $W^1$ is $(CR^{24}R^{25})_n$ (wherein each of $R^{24}$ and $R^{25}$ is independently a hydrogen atom or a $C_{1-6}$ alkyl group, (the $C_{1-6}$ alkyl group may be substituted with one or more halogen atoms), and n is 0, 1, 2 or 3), an oxygen atom, a sulfur atom or $NR^{36}$ (wherein $R^{36}$ is a hydrogen atom, a $C_{1-6}$ alkyl group, a formyl group or a $C_{1-6}$ alkylcarbonyl group), each of $W^2$ and $W^3$ is independently a hydrogen atom or a $C_{1-3}$ alkyl group (the $C_{1-3}$ alkyl group may be substituted with one or more halogen atoms), m is 0, 1, 2 or 3, and $W^4$ is a hydroxyl group, a thiol group, an amino group, a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkylcarbonylamino group, a mono- or di-$C_{1-10}$ alkylamino group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkylcarbonylamino group and the mono- or di-$C_{1-10}$ alkylamino group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a thiol group, a phosphonic acid group, a sulfonic acid group, a tetrazole group, a $C_{2-14}$ aryl group and a $C_{2-14}$ aryloxy group), $SO_2R^{28}$, $SOR^{28}$, $COR^{28}$ (wherein $R^{28}$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, $C_{1-10}$ alkylcarbonyloxy group, a $C_{1-10}$ alkoxycarbonyl group, $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group, a $C_{2-14}$ aryloxy group (the $C_{2-14}$ aryl group and the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^{29}R^{30}$ (wherein each of $R^{29}$ and $R^{30}$ is independently a hydrogen atom, a hydroxyl group, a formyl group, a cyano group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{1-6}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^{29}$ and $R^{30}$, together with each other means —$(CH_2)_{m3}$-G-$(CH_2)_{m4}$— (wherein G is an oxygen atom, a sulfur atom, a $CR^{31}R^{32}$ (wherein each of $R^{31}$ and $R^{32}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^{33}$ (wherein $R^{33}$ is a hydrogen atom, a hydroxyl group, a formyl group, a $C_{1-10}$ alkyl group, a $C_{2-6}$ alkenyl group, $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m3 and m4 is independently an integer of from 0 to 5, provided that m3+m4 is 3, 4 or 5))), a tetrazole group, or a phosphonic acid group)).

(2) The method for expanding CD34+ cells according to (1), wherein A is a nitrogen atom, and B is a sulfur atom.

(3) The method for expanding CD34+ cells according to (1), wherein A is a nitrogen atom, and B is an oxygen atom.

(4) The method for expanding CD34+ cells according to (1), wherein A is a nitrogen atom, and B is $NR^9$ (wherein $R^9$ is a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)).

(5) The method for expanding CD34$^+$ cells according to (1), wherein A is CR$^4$ (wherein R$^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), SO$_2$R$^5$, SOR$^5$ or COR$^5$ (wherein R$^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or NR$^6$R$^7$ (wherein each of R$^6$ and R$^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is a oxygen atom.

(6) The method for expanding $CD34^+$ cells according to (1), wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyloxy group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^6$ and $R^7$ mean, together with each other, —$(CH_2)_{m1}$-E-$(CH_2)_{m2}$— (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is sulfur atom.

(7) The method for expanding $CD34^+$ cells according to (1), wherein A is $CR^4$ (wherein $R^4$ is a hydrogen atom, a hydroxyl group (the hydroxyl group may be substituted with a $C_{2-6}$ alkenyl or a $C_{2-6}$ alkynyl group), a thiol group (the thiol group may be substituted with a $C_{1-10}$ alkyl group, a $C_{2-6}$ alkenyl group, a $C_{2-6}$ alkynyl group or a $C_{1-10}$ alkylcarbonyl group), an amino group (the amino group may be substituted with one or two $C_{2-6}$ alkenyl groups or one or two $C_{2-6}$ alkynyl groups), a formyl group, a halogen atom, a nitro group, a cyano group, a $C_{1-10}$ alkyl group, a $C_{2-6}$ alkenyl group, a $C_{2-6}$ alkynyl group, a $C_{1-10}$ alkylcarbonyl group, a $C_{1-10}$ alkylcarbonylamino group, a mono- or di-$C_{1-10}$ alkylamino group, a $C_{1-10}$ alkoxy group (the $C_{1-10}$ alkyl group, the $C_{2-6}$ alkenyl group, the $C_{2-6}$ alkynyl group, the $C_{1-10}$ alkylcarbonyl group, the $C_{1-10}$ alkylcarbonylamino group, the mono- or di-$C_{1-10}$ alkylamino group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), $SO_2R^5$, $SOR^5$ or $COR^5$ (wherein $R^5$ is a hydroxyl group, a $C_{1-10}$ alkyl group, a $C_{2-6}$ alkenyl group, a $C_{2-6}$ alkynyl group, a $C_{1-10}$ alkoxy group (the $C_{1-10}$ alkyl group, the $C_{2-6}$ alkenyl group, the $C_{2-6}$ alkynyl group and the $C_{1-10}$ alkoxy group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or $NR^6R^7$ (wherein each of $R^6$ and $R^7$ is independently a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group), or $R^6$ and $R^7$ mean, together with each other, $-(CH_2)_{m1}-E-(CH_2)_{m2}-$ (wherein E is an oxygen atom, a sulfur atom, $CR^{26}R^{27}$ (wherein each of $R^{26}$ and $R^{27}$ is independently a hydrogen atom, a $C_{1-10}$ alkyl group, a $C_{2-14}$ aryl group, a $C_{1-10}$ alkoxy group, a $C_{2-14}$ aryloxy group, a hydroxyl group or a protected hydroxyl group) or $NR^8$ (wherein $R^8$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)), and each of m1 and m2 is independently an integer of from 0 to 5 provided that m1+m2 is 3, 4 or 5)))), and B is $NR^9$ (wherein $R^9$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)), a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group) or a $C_{2-14}$ aryloxy group (the $C_{2-14}$ aryloxy group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)).

(8) The method for expanding CD34+ cells according to any one of (1) to (7), wherein $L^1$ is a bond.

(9) The method for expanding CD34+ cells according to any one of (1) to (8), wherein $L^2$ is a bond.

(10) The method for expanding CD34+ cells according to any one of (1) to (9), wherein $L^3$ is $NR^{19}$ (wherein $R^{19}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkylcarbonyloxy group, the $C_{1-10}$ alkoxycarbonyl group, the $C_{1-10}$ alkoxy group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)).

(11) The method for expanding CD34$^+$ cells according to any one of (1) to (9), wherein $L^3$ is NH.

(12) The method for expanding CD34$^+$ cells according to (10) or (11), wherein $L^4$ is $NR^{22}$ (wherein $R^{22}$ is a hydrogen atom, a hydroxyl group, a formyl group, a $C_{1-10}$ alkyl group, a $C_{2-6}$ alkenyl group, a $C_{2-6}$ alkynyl group, a $C_{1-10}$ alkoxy group, a $C_{1-10}$ alkylcarbonyloxy group, a $C_{1-10}$ alkoxycarbonyl group, a $C_{1-10}$ alkylcarbonyl group (the $C_{1-10}$ alkyl group, the $C_{2-6}$ alkenyl group, the $C_{2-6}$ alkynyl group, the $C_{1-10}$ alkoxy group, the $C_{1-10}$ alkylcarbonyloxy group, the $C_{1-10}$ alkoxycarbonyl group and the $C_{1-10}$ alkylcarbonyl group may be optionally substituted with one or more substituents selected from the group consisting of: a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group (the $C_{2-14}$ aryl group and the $C_{2-14}$ aryloxy group may be substituted with one or more $C_{1-6}$ alkyl groups (the $C_{1-6}$ alkyl group may be substituted with one or more halogen atoms) or one or more halogen atoms)) or a $C_{2-14}$ aryl group (the $C_{2-14}$ aryl group may be optionally substituted with one or more substituents selected from the group consisting of: a $C_{1-10}$ alkyl group (the $C_{1-10}$ alkyl group may be substituted with one or more halogen atoms), a $C_{2-6}$ alkenyl group, a $C_{2-6}$ alkynyl group, a carboxyl group, a nitro group, a cyano group, a halogen atom, a $C_{1-10}$ alkoxy group, a $C_{1-10}$ alkylcarbonyl group, a $C_{1-10}$ alkylcarbonyloxy group, a $C_{1-10}$ alkoxycarbonyl group, a $C_{1-10}$ alkylcarbonylamino group, an amino group, a mono- or di-$C_{1-10}$ alkylamino group, a hydroxyl group, a protected hydroxyl group, a $C_{2-14}$ aryl group and a $C_{2-14}$ aryloxy group)).

(13) The method for expanding CD34$^+$ cells according to (10) or (11), wherein $L^4$ is NH.

(14) The method for expanding CD34$^+$ cells according to (10) or (11), wherein $L^4$ is a bond.

(15) The method for expanding CD34$^+$ cells according to (12), (13) or (14), wherein Y is an oxygen atom.

(16) The method for expanding CD34$^+$ cells according to (12), (13) or (14), wherein Y is a sulfur atom.

(17) The method for expanding CD34$^+$ cells according to (15) or (16), wherein X is a hydroxyl group.

(18) The method for expanding CD34$^+$ cells according to (15), (16) or (17), wherein $R^3$ is a $C_{2-14}$ aryl group (the $C_{2-14}$ aryl group is optionally substituted with one or more substituents selected from the group consisting of: a hydroxyl group, an amino group, a carboxyl group, a phosphonic acid group, a sulfonic acid group, a carbamido group, a sulfamido group, a tetrazole group and a $C_{1-10}$ alkoxycarbonyl group).

(19) The method for expanding CD34$^+$ cells according to (15), (16) or (17), wherein $R^3$ is a $C_{2-14}$ aryl group substituted with a group represented by the formula (2) (wherein $R^{37}$ is a 2-pyridyl group, a 3-pyridyl group, a 4-pyridyl group, a 2-pyridylmethyl group, a 3-pyridylmethyl group, a 4-pyridylmethyl group or an N-oxide thereof or a hydroxyl group).

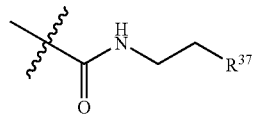

(2)

(20) The method for expanding CD34$^+$ cells according to (15), (16) or (17), wherein $R^3$ is a $C_{2-14}$ aryl group (the $C_{2-14}$ aryl group is optionally substituted with one or more substituents selected from the group consisting of: a hydroxyl group, an amino group, a carboxyl group, a phosphonic acid group, a sulfonic acid group, a carbamido group, a sulfamido group, a tetrazole group and a $C_{1-10}$ alkoxycarbonyl group and one or more substituents selected from the group consisting of: a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group).

(21) The method for expanding CD34$^+$ cells according to any one of (1) to (20), which involves addition of at least one blood cell stimulating factor.

(22) The method for expanding CD34$^+$ cells according to (21), wherein the blood cell stimulating factor is selected from the group consisting of stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO) and erythropoietin (EPO).

(23) The method for expanding CD34$^+$ cells according to (22), wherein the blood cell stimulating factor is stem cell factor (SCF).

(24) The method for expanding CD34$^+$ cells according to any one of (1) to (23), wherein the CD34$^+$ cells are obtained from the bone marrow, the liver, the spleen or peripheral or cord blood.

(25) The method for expanding CD34$^+$ cells according to (24), wherein the CD34$^+$ cells are obtained from cord blood.

(26) The method for expanding CD34$^+$ cells according to (25), wherein CD34$^+$ cells obtained from cord blood are cultured in the presence of stem cell factor (SCF).

(27) CD34$^+$ cells expanded by the method as defined in any one of (1) to (26).

(28) A material for cell therapy by transplanting CD34$^+$ cells expanded by the method as defined in any one of (1) to (26) into a human for treatment of a disease.

(29) The material for cell therapy according to (28), wherein the disease to be treated is leukemia, aplastic anemia, myelodysplastic syndrome, malignant lymphoma, multiple myeloma, myeloproliferative disease, a genetic blood disease, a solid tumor, an autoimmune disease, immunodeficiency, cerebral infarction, myocardial infarction or obstructive arteriosclerosis.

Effects of the Invention

According to the method of the present invention, it is possible to expand CD34+ cells by culturing them ex vivo. CD34+ cells expanded by the method of the present invention are rich in hematopoietic stem cells and hematopoietic progenitor cells can be used as a cell transplant for treatment of diseases. The method of the present invention also makes it possible to provide a cell transplant (graft) soon as required even from a transplant source which can be obtained in a limited amount, by expanding cell populations of hematopoietic stem cells and hematopoietic progenitor cells easily.

The low molecular weight compound to be used in the present invention can be produced by an ordinary process for organic synthesis and is obtained without using any substances from an animal other than human or a microorganism. Therefore, it is possible to prevent contamination with an unknown pathogen or a biomaterial from an animal other than human or a microorganism, as compared with expansion of hematopoietic stem cells using a protein such as cytokines and growth factors obtained by gene recombination technology.

Namely, CD34+ cells obtained by the method of the present invention can avoid infection, contamination with foreign genes or immune response to foreign proteins. While being proteins, cytokines and growth factors can be stored or used within very narrow optimal ranges in terms of pH, heat and ion strength, the low molecular weight compound in the present invention can be used and stored under relatively broad ranges of conditions. In addition, because the low molecular weight compound in the present invention can be produced inexpensively and continuously unlike proteins, it is possible to eventually reduce treatment cost.

BEST MODE FOR CARRYING OUT THE INVENTION

Now, the present invention will be described in further detail.

The terms used herein are defined as follows.

Hematopoietic stem cells are defined as cells having both pluripotency which allows them to differentiate into blood cells of all lineages and the ability to regenerate themselves while maintaining the pluripotency. Multipotential hematopoietic progenitor cells are cells which can differentiate into a plurality of blood cell lineages, though not into all blood cell lineages, but have no self-renewal ability. Unipotential hematopoietic progenitor cells are cells which can differentiate into only one blood cell lineage and have no self-renewal ability. Hematopoietic progenitor cells are a group of cells which covers both multipotential and unipotential hematopoietic progenitor cells. For example, the hematopoietic progenitor cells in the present invention may be granulocyte-macrophage colony forming cells (CFU-GM), eosinophil colony forming cells (EO-CFC), erythroid burst forming cells (BFU-E) as erythroid progenitor cells, megakaryocyte colony forming cells (CFU-MEG) or myeloid stem cells (mixed colony forming cells, CFU-GEMM).

CD34+ means expressing CD (cluster of differentiation) 34 antigen on the cell surface. This antigen is a marker for hematopoietic stem cells and/or hematopoietic progenitor cells and disappears as the cell differentiates. Populations of CD34+ cells are enriched with hematopoietic stem cells and hematopoietic progenitor cells.

The low molecular weight compound used in the present invention acts on hematopoietic stem cells and/or hematopoietic progenitor cells and shows such an activity that it helps CD34+ cells proliferate and survive when they are cultured ex vivo. The low molecular weight compound is capable of proliferate hematopoietic stem cells with minimal differentiation. In some cases of treatment by transplantation of hematopoietic stem cells such as peripheral stem cells and cord blood stem cells, hematopoietic stem cells and hematopoietic progenitor cells as the transplant cannot be obtained in sufficient numbers to carry out the transplantation. Use of the low molecular weight compound makes it possible to expand CD34+ cells ex vivo and obtain hematopoietic stem cells and hematopoietic progenitor cells in the amount required to carry out the transplantation even in such cases. Specifically speaking, it is possible to expand CD34+ cells with minimal differentiation by culturing them in a medium containing the low molecular weight compound and use them for transplantation. It is also possible to expand CD34+ cells more efficiently by further adding various cytokines or growth factors, by coculturing them with stromal cells, or by further adding other low molecular weight compounds which act on CD34+ cells.

In the method of the present invention, the collected cells to be cultured for transplantation may be an isolated population of either hematopoietic stem cells or hematopoietic progenitor cells or a population containing both of them. The cells may contain either hematopoietic stem cells or hematopoietic progenitor cells and further contain other mature blood cells.

The source of the CD34+ cells in the method of the present invention may be any tissue as long as it contains hematopoietic stem cells, and it may be human bone marrow, peripheral blood, peripheral blood containing hematopoietic stem cells mobilized by a cytokine, spleen, liver or cord blood.

The CD34+ cells can be cultured in a culture vessel generally used for animal cell culture such as a Petri dish, a flask, a plastic bag, a Teflon (registered trademark) bag, optionally after preliminary coating with an extracellular matrix or a cell adhesion molecule. The material for such a coating may be collagens I to XIX, fibronectin, vitronectin, laminins 1 to 12, nitrogen, tenascin, thrombospondin, von Willebrand factor, osteoponin, fibrinogen, various elastins, various proteoglycans, various cadherins, desmocolin, desmoglein, various integrins, E-selectin, P-selectin, L-selectin, immunoglobulin superfamily, Matrigel, poly-D-lysine, poly-L-lysine, chitin, chitosan, Sepharose, alginic acid gel, hydrogel or a fragment thereof. Such a coating material may be a recombinant material having an artificially modified amino acid sequence. The CD34+ cells may be cultured by using a bioreactor which can mechanically control the medium composition, pH and the like and obtain high density culture (Schwartz R M, Proc. Natl. Acad. Sci. U.S.A., 88:6760, 1991; Koller M R, Bone Marrow Transplant, 21:653, 1998; Koller, M R, Blood, 82:378, 1993; Astori G, Bone Marrow Transplant, 35: 1101, 2005).

The nutrient medium to be used in the method of the present invention may be a natural medium, a semi-synthetic medium or a synthetic medium in terms of composition, and may be a solid medium, a semisolid medium or a liquid medium in terms of shape, and any nutrient medium used for animal cell culture, especially for hematopoietic stem cell and/or hematopoietic progenitor cell culture, may be used. As such a nutrient medium, Dulbecco's Modified Eagles's Medium (DMEM), Ham's Nutrient Mixture H12 Mixture F12, McCoy's 5A medium, Eagles's Minimum Essential Medium (EMEM), RPMI1640 medium, Isocove's Modified Dulbecco's Medium (IMDM), StemPro34 (Invitrogen), X-VIVO 10 (Cambrex), X-VIVO 15 (Cambrex), HPGM (Cambrex), StemSpan H3000 (Stemcell Technologies), StemSpan SFEM (Stemcell Technologies), Stemline II (Sigma-Aldrich) or QBSF-60 (Quality Biological) may be mentioned.

Such a medium may contain sodium, potassium, calcium, magnesium, phosphorus, chlorine, amino acids, vitamins, cytokines, hormones, antibiotics, serum, fatty acids, saccharides or the like. In the culture, other chemical components or biological components may be incorporated singly or in combination, as the case requires. Such components to be incorporated in the medium may be fetal calf serum, human serum, horse serum, insulin, transfferin, lactoferrin, cholesterol, ethanolamine, sodium selenite, monothioglycerol, 2-mercaptoethanol, bovine serum albumin, sodium pyruvate, polyethylene glycol, various vitamins, various amino acids, agar, agarose, collagen, methylcellulose, various cytokines, various growth factors or the like. The cytokines to be added to the medium may be interleukin 1 (IL-1), interleukin 2 (IL-2), interleukin 3 (IL-3), interleukin 4 (IL-4), interleukin 5 (IL-5), interleukin 6 (IL-6), interleukin 7 (IL-7), interleukin 8 (IL-8), interleukin 9 (IL-9), interleukin 10 (IL-10), interleukin 11 (IL-11), interleukin 12 (IL-12), interleukin 13 (IL-13), interleukin 14 (IL-14), interleukin 15 (IL-15), interleukin 18 (IL-18), interleukin 21 (IL-21), interferon-α (IFN-α), interferon-β (IFN-β), interferon-γ (IFN-γ), granulocyte colony stimulating factor (G-CSF), monocyte colony stimulating factor (M-CSF), granulocyte-macrophage colony stimulating factor (GM-CSF), stem cell factor (SCF), flk2/flt3 ligand (FL), leukemia inhibitory factor (LIF), oncostatin M (OM), erythropoietin (EPO) and thrombopoietin (TPO), but are not restricted to those mentioned above. The growth factors to be added to the medium may be transforming growth factor-β (TGF-β), macrophage inflammatory protein-1α (MIP-1α), epidermal growth factor (EGF), fibroblast growth factor (FGF), nerve growth factor (NGF), hepatocyte growth factor (HGF), protease nexin I, protease nexin II, platelet-derived growth factor (PDGF), cholinergic differentiation factor (CDF), chemokines, Notch ligand (such as Delta 1) and Wnt protein, but are not restricted to those mentioned above. Besides, recombinant cytokines or growth factors having an artificially modified amino acid sequence such as IL-6/soluble IL-6 receptor complex, and Hyper IL-6 (IL-6/soluble IL-6 receptor fusion protein) may also be added.

Among the above-mentioned cytokines and growth factors, preferred are stem cell factor (SCF), interleukin 3 (IL-3), interleukin 6 (IL-6), interleukin 11 (IL-11), flk2/flt3 ligand (FL), granulocyte colony stimulating factor (G-CSF), granulocyte-macrophage colony stimulating factor (GM-CSF), thrombopoietin (TPO), erythropoietin (EPO), Notch ligand (Delta 1) and the like, and more preferred are stem cell factor (SCF), flk2/flt3 ligand (FL), thrombopoietin (TPO) and the like.

Cytokines and growth factors are usually added to culture at a concentration of 0.1 ng/mL to 1000 ng/mL, preferably from 1 ng/mL to 100 ng/mL.

In addition, at least one chemical substance known to be effective for expansion of hematopoietic stem cells may be added to the medium singly or in combination. Examples of such substances include copper chelators represented by tetraethylenepentamine, histone deacetylase inhibitors represented by trichostain A, DNA methylase inhibitors represented by 5-aza-2'-deoxycytidine, retinoic acid receptor ligands represented by all-trans retinoic acid, aldehyde dehydrogenase inhibitors represented by dimethylaminobenzaldehyde, but they are not restricted to those mentioned above.

The chemical components and biological components mentioned above may be used not only by adding them to the medium but also by immobilizing them onto the surface of the substrate or support used for the culture, specifically speaking, by dissolving a component to be used in an appropriate solvent, coating the substrate or support with the resulting solution and then washing away an excess of the component. Such a component to be used may be added to the substrate or support preliminarily coated with a substance which binds to the component.

When the low molecular weight compound of the present invention is added to such a medium as mentioned above, it is first dissolved in an appropriate solvent and added to the medium so that the concentration of the compound will be from 1 ng/mL to 100 µg/mL, preferably from 2 ng/mL to 50 µg/mL, more preferably from 20 ng/mL to 10 µg/mL, particularly preferably from 300 ng/mL to 3 µg/mL. Examples of the appropriate solvent include dimethyl sulfoxide (DMSO) and various alcohols, but it is not restricted thereto. The low molecular weight compound of the present invention may be immobilized on the surface of the substrate or support used for the culture. The low molecular weight compound of the present invention may be provided or stored in a certain form, for example, in a solid form as a tablet, a pill, a capsule or a granule, in a liquid form as a solution or suspension in an appropriate solvent or resolvent, or in the form bound to the substrate or support. When it is formulated into such a form, additives such as a preservative like p-hydroxybenzoates, an excipient like lactose, glucose, sucrose and mannitol; a lubricant like magnesium stearate and talc; a binder like polyvinyl alcohol, hydroxypropylcellulose and gelatin, a surfactant like fatty acid esters, a plasticizer like glycerin may be added. The additives are not restricted to those mentioned above and a person skilled in the art can use any additives of choice.

The $CD34^+$ cells are cultured usually at a temperature of from 25 to 39° C., preferably from 33 to 39° C., in the atmosphere having a $CO_2$ concentration of from 4 to 10 vol %, preferably from 4 to 6 vol %, usually for a period of from 3 to 35 days, preferably from 5 to 21 days, more preferably from 7 to 14 days.

In the method of the present invention, when the $CD34^+$ cells are cocultured with stromal cells, collected bone marrow cells may be grown directly in culture. Alternatively, it is possible to separate collected bone marrow into stromal cells, $CD34^+$ cells, and coculture the $CD34^+$ cells with stromal cells from an individual other than the bone marrow donor. It is also possible to first grow stromal cells only and add and grow $CD34^+$ cells in coculture in such a medium under such conditions as mentioned above.

$CD34^+$ cells expanded by the method of the present invention can be used as a cell transplant. Because hematopoietic stem cells can differentiate into blood cells of all lineages, they may be transplanted after differentiated into a certain type of blood cells ex vivo. $CD34^+$ cells expanded by the method of the present invention may be transplanted as they are, or after enrichment using a cell surface antigen as an index, for example, by a magnetic bead method or by a cell sorting method. Such a cell surface antigen molecule may be CD2, CD3, CD4, CD8, CD13, CD14, CD15, CD16, CD19, CD24, CD33, CD34, CD38, CD41, CD45, CD56, CD66, CD90, CD133 or glycophorin A, but is not restricted thereto. The expanded $CD34^+$ cells may be transplanted to its donor or another individual.

Namely, $CD34^+$ cells expanded by the method of the present invention can be used as a transplant for hematopoietic stem cell therapy as a substitute for conventional bone marrow or cord blood transplantation. The transplantation of $CD34^+$ cells expanded by using the low molecular compound of the present invention is carried out in the same manner as conventional bone marrow or cord blood transplantation, except for the cells to be used. The transplant may be a composition containing a buffer solution, an antibiotic, a pharmaceutical in addition to CD34+ cells expanded by the method of the present invention.

The CD34+ cell transplant obtained by the method of the present invention is useful for treatment of not only various types of leukemia but also various diseases. For example, in a case of treatment of a solid cancer patient by chemotherapy or radiotherapy which may cause myelosuppression as a side effect, the patient can recover from hematopoietic damage quickly if the CD34+ cells in bone marrow collected from the patient preliminarily to the treatment are expanded ex vivo and returned to the patient after the treatment. Thus, a more intense chemotherapy becomes available with an improved therapeutic effect. It is also possible to alleviate a deficiency in a certain type of blood cells in a patient by differentiating CD34+ cells obtained by the method of the present invention into such a type of blood cells and returning them into the patient. The method of the present invention is effective against diseases accompanying decrease in hematopoietic cells and/or hematopoietic insufficiency, diseases accompanying increase in hematopoietic cells, diseases accompanying hematopoietic dysfunction, decrease in immunocytes, increase in immunocytes, diseases accompanying autoimmunity, immune dysfunction and ischemic diseases.

As specific examples, chronic granulomatosis, severe combined immunodeficiency syndrome, adenylate deaminase (ADA) deficiency, agammaglobulinemia, Wiskott-Aldrich syndrome, Chediak-Higashi syndrome, immunodeficiency syndrome such as acquired immunodeficiency syndrome (AIDS), C3 deficiency, congenital anemia such as thalassemia, hemolytic anemia due to enzyme deficiency and sicklemia, lysosomal storage disease such as Gaucher's disease and mucopolysaccharidosis, adrenoleukodystrophy, various kinds of cancers and tumors, especially blood cancers such as acute or chronic leukemia, Fanconi syndrome, aplastic anemia, malignant lymphoma, Hodgkin's disease, multiple myeloma, chronic hepatopathy, renal failure, massive blood transfusion of bank blood or during operation, hepatitis B, hepatitis C, severe infections, systemic lupus erythematodes, articular rheumatism, xerodermosteosis, systemic sclerosis, polymyositis, dermatomyositis, mixed connective tissue disease, polyarteritis nodosa, Hashimoto's disease, Basedow's disease, myasthenia gravis, insulin dependent diabetes mellitus, autoimmune hemolytic anemia, snake bite, hemolytic uremic syndrome, hypersplenism, bleeding, Bernard-Soulier syndrome, Glanzmann's thrombasthenia, uremia, myelodysplastic syndrome, polycythemia rubra vera, erythremia, essential thrombocythemia, myeloproliferative disease, cerebral infarction, myocardial infarction, obstructive arteriosclerosis and the like may be mentioned.

Preferred embodiments of expansion of CD34+ cells and transplantation of the expanded CD34+ cells according to the present invention will be described below.

First, for expansion of CD34+ cells, cord blood, bone marrow, peripheral blood or the like is collected, and a cell population enriched with CD34+ cells is separated from it. CD34+ cells can be separated by density centrifugation combined with magnetic cell sorting (MACS) or flow cytometry. For example, CPD (citrate-phosphate-dextran)-treated blood is fractioned by density centrifugation to separate and collect a mononuclear cell enriched fraction (hereinafter referred to as nucleated cell fraction). As density centrifugation, dextran or Ficoll density centrifugation, Ficoll-paque density gradient centrifugation, Percoll discontinuous density gradient centrifugation or Lymphoprep density gradient centrifugation may be mentioned. Then, magnetic beads coated with an anti-human CD34 monoclonal antibody (Miltenyi Biotec; hereinafter referred to as CD34 antibody magnetic beads) and the collected nucleated cell fraction are mixed and incubated at from 2 to 8° C. (for about 30 minutes) to bind CD34+ cells to the antibody magnetic beads. The antibody magnetic bead/CD34+ cell complexes are separated and collected by a specialized magnetic cell separator such as autoMACS system (Miltenyi Biotec). The CD34+ cells thus obtained are cultured using the low molecular weight compound of the present invention. The conditions, incubator and medium for culturing CD34+ cells, the species and amount of the low molecular weight compound, the kinds and amounts of additives and the incubation time and temperature may be selected appropriately from those disclosed herein by the person in charge, but are not restricted thereto.

After culturing, the total cell count is measured by trypan blue assay, Flow-Count™ fluorosphere assay or the like, while the cell culture is stained with an anti CD34 antibody labeled with a fluorescent dye such as FITC (fluorescein isothiocyanate), PE (phycoerythrin) or APC (allophycocyanin), and the proportion of CD34+ cells is analyzed by flow cytometry. Thus, it is possible to determine how much CD34+ cells are expanded in the cell culture. Expanded CD34+ cells may be infused by drip, for example, in the case of treatment of leukemia, into patients pretreated with an anticancer drug, total body irradiation or an immunosuppressive drug for eradication of cancer cells or for facilitation of donor cell engraftment. The disease to be treated, the pretreatment and the cell transplantation method are selected appropriately by the person in charge. The engraftment of transplanted hematopoietic stem cells and/or hematopoietic progenitor cells in the recipient, the recovery of hematopoiesis, the presence of side effects of the transplantation and the therapeutic effect of the transplantation can be judged by an ordinary assay used in transplantation therapy.

As described above, the present invention makes it possible to expand hematopoietic stem cells and/or hematopoietic progenitor cells and to carryout transplantation therapy and gene therapy safely and easily in a short term by using the expanded cells.

Now, the compound to be used in the present invention will be described in terms of the definitions of terms used for it and its best mode.

In the present invention, "n" denotes normal, "i" denotes iso, "s" denotes secondary, "t" denotes tertiary, "c" denotes cyclo, "o" denotes ortho, "m" denotes meta, "p" denotes para, "Ph" denotes phenyl, "Py" denotes pyridyl, "Naphthyl" denotes naphthyl, "Me" denotes methyl, "Et" denotes ethyl, "Pr" denotes propyl, and "Bu" denotes butyl.

First, the terms in the respective substituents $R^1$ to $R^{37}$ will be explained.

As a halogen atom, a fluorine atom, a chlorine atom, a bromine atom or an iodine atom may be mentioned.

A $C_{1-3}$ alkyl group may be linear, branched or a $C_3$ cycloalkyl group, and methyl, ethyl, n-propyl, i-propyl and c-propyl and the like may be mentioned.

A $C_{1-6}$ alkyl group may be linear, branched or a $C_{3-6}$ cycloalkyl group, and as specific examples, in addition to those mentioned above, n-butyl, i-butyl, s-butyl, t-butyl, c-butyl, 1-methyl-c-propyl, 2-methyl-c-propyl, n-pentyl, 1-methyl-n-butyl, 2-methyl-n-butyl, 3-methyl-n-butyl, 1,1-dimethyl-n-propyl, 1,2-dimethyl-n-propyl, 2,2-dimethyl-n-propyl, 1-ethyl-n-propyl, c-pentyl, 1-methyl-c-butyl, 2-methyl-c-butyl, 3-methyl-c-butyl, 1,2-dimethyl-c-propyl, 2,3-dimethyl-c-propyl, 1-ethyl-c-propyl, 2-ethyl-c-propyl, n-hexyl, 1-methyl-n-pentyl, 2-methyl-n-pentyl, 3-methyl-n-pentyl, 4-methyl-n-pentyl, 1,1-dimethyl-n-butyl, 1,2-dimethyl-n-butyl, 1,3-dimethyl-n-butyl, 2,2-dimethyl-n-butyl, 2,3-dimethyl-n-butyl, 3,3-dimethyl-n-butyl, 1-ethyl-n-butyl, 2-ethyl-n-butyl, 1,1,2-trimethyl-n-propyl, 1,2,2-trimethyl-n-propyl, 1-ethyl-1-methyl-n-propyl, 1-ethyl-2-methyl-n-propyl, c-hexyl, 1-methyl-c-pentyl, 2-methyl-c-pentyl, 3-methyl-c-pentyl, 1-ethyl-c-butyl, 2-ethyl-c-butyl, 3-ethyl-c-butyl, 1,2-dimethyl-c-butyl, 1,3-dimethyl-c-butyl, 2,2-dimethyl-c-butyl, 2,3-dimethyl-c-butyl, 2,4-dimethyl-c-butyl, 3,3-dimethyl-c-butyl, 1-n-propyl-c-propyl, 2-n-propyl-c-propyl, 1-i-propyl-c-propyl, 2-i-propyl-c-propyl, 1,2,2-trimethyl-c-propyl, 1,2,3-trimethyl-c-propyl, 2,2,3-trimethyl-c-propyl, 1-ethyl-2-methyl-c-propyl, 2-ethyl-1-methyl-c-propyl, 2-ethyl-2-methyl-c-propyl, 2-ethyl-3-methyl-c-propyl and the like may be mentioned.

A $C_{1-10}$ alkyl group may be linear, branched or a $C_{3-10}$ cycloalkyl group, and as specific examples, in addition to those mentioned above, 1-methyl-1-ethyl-n-pentyl, 1-heptyl, 2-heptyl, 1-ethyl-1,2-dimethyl-n-propyl, 1-ethyl-2,2-dimethyl-n-propyl, 1-octyl, 3-octyl, 4-methyl-3-n-heptyl, 6-methyl-2-n-heptyl, 2-propyl-1-n-heptyl, 2,4,4-trimethyl-1-n-pentyl, 1-nonyl, 2-nonyl, 2,6-dimethyl-4-n-heptyl, 3-ethyl-2,2-dimethyl-3-n-pentyl, 3,5,5-trimethyl-1-n-hexyl, 1-decyl, 2-decyl, 4-decyl, 3,7-dimethyl-1-n-octyl, 3,7-dimethyl-3-n-octyl and the like may be mentioned.

As a $C_{2-6}$ alkynyl group, ethynyl, 1-propynyl, 2-propynyl, 1-butynyl, 2-butynyl, 3-butynyl, 1-methyl-2-propynyl, 1-pentynyl, 2-pentynyl, 3-pentynyl, 4-pentynyl, 1-methyl-2-butynyl, 1-methyl-3-butynyl, 2-methyl-3-butynyl, 3-methyl-1-butynyl, 1,1-dimethyl-2-propynyl, 2-ethyl-e-propyl, 1-hexynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-1-pentynyl, 3-methyl-4-pentynyl, 4-methyl-1-pentynyl, 4-methyl-2-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 1-n-propyl-2-propynyl, 2-ethyl-3-butynyl, 1-methyl-1-ethyl-2-propynyl, 1-i-propyl-2-propynyl and the like may be mentioned.

A $C_{2-6}$ alkenyl group may be linear, branched or a $C_{3-6}$ cycloalkenyl group, and ethenyl, 1-propenyl, 2-propenyl, 1-methyl-1-ethenyl, 1-butenyl, 2-butenyl, 3-butenyl, 2-methyl-1-propenyl, 2-methyl-2-propenyl, 1-ethylethenyl, 1-methyl-1-propenyl, 1-methyl-2-propenyl, 1-pentenyl, 2-pentenyl, 3-pentenyl, 4-pentenyl, 1-n-propylethenyl, 1-methyl-1-butenyl, 1-methyl-2-butenyl, 1-methyl-3-butenyl, 2-ethyl-2-propenyl, 2-methyl-1-butenyl, 2-methyl-2-butenyl, 2-methyl-3-butenyl, 3-methyl-1-butenyl, 3-methyl-2-butenyl, 3-methyl-3-butenyl, 1,1-dimethyl-2-propenyl, 1-i-propylethenyl, 1,2-dimethyl-1-propenyl, 1,2-dimethyl-2-propenyl, 1-c-pentenyl, 2-c-pentenyl, 3-c-pentenyl, 1-hexenyl, 2-hexenyl, 3-hexenyl, 4-hexenyl, 5-hexenyl, 1-methyl-1-pentenyl, 1-methyl-2-pentenyl, 1-methyl-3-pentenyl, 1-methyl-4-pentenyl, 1-n-butylethenyl, 2-methyl-1-pentenyl, 2-methyl-2-pentenyl, 2-methyl-3-pentenyl, 2-methyl-4-pentenyl, 2-n-propyl-2-propenyl, 3-methyl-1-pentenyl, 3-methyl-2-pentenyl, 3-methyl-3-pentenyl, 3-methyl-4-pentenyl, 3-ethyl-3-butenyl, 4-methyl-1-pentenyl, 4-methyl-2-pentenyl, 4-methyl-3-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1-methyl-2-ethyl-2-propenyl, 1-s-butylethenyl, 1,3-dimethyl-1-butenyl, 1,3-dimethyl-2-butenyl, 1,3-dimethyl-3-butenyl, 1-i-butylethenyl, 2,2-dimethyl-3-butenyl, 2,3-dimethyl-1-butenyl, 2,3-dimethyl-2-butenyl, 2,3-dimethyl-3-butenyl, 2-i-propyl-2-propenyl, 3,3-dimethyl-1-butenyl, 1-ethyl-1-butenyl, 1-ethyl-2-butenyl, 1-ethyl-3-butenyl, 1-n-propyl-1-propenyl, 1-n-propyl-2-propenyl, 2-ethyl-1-butenyl, 2-ethyl-2-butenyl, 2-ethyl-3-butenyl, 1,1,2-trimethyl-2-propenyl, 1-t-butylethenyl, 1-methyl-1-ethyl-2-propenyl, 1-ethyl-2-methyl-1-propenyl, 1-ethyl-2-methyl-2-propenyl, 1-i-propyl-1-propenyl, 1-i-propyl-2-propenyl, 1-methyl-2-c-pentenyl, 1-methyl-3-c-pentenyl, 2-methyl-1-c-pentenyl, 2-methyl-2-c-pentenyl, 2-methyl-3-c-pentenyl, 2-methyl-4-c-pentenyl, 2-methyl-5-c-pentenyl, 2-methylene-c-pentyl, 3-methyl-1-c-pentenyl, 3-methyl-2-c-pentenyl, 3-methyl-3-c-pentenyl, 3-methyl-4-c-pentenyl, 3-methyl-5-c-pentenyl, 3-methylene-c-pentyl, 1-c-hexenyl, 2-c-hexenyl, 3-c-hexenyl and the like may be mentioned.

A $C_{2-14}$ aryl group may be a $C_{6-14}$ aryl group containing no hetero atoms as ring constituting atoms, a $C_{2-9}$ aromatic heterocyclic group or a $C_{2-14}$ fused polycyclic group, and a $C_{2-9}$ aromatic heterocyclic group may be a 5 to 7-membered $C_{2-6}$ heteromonocyclic group or 8 to 10-membered $C_{5-9}$ fused heterobicyclic group containing from 1 to 3 oxygen atoms, nitrogen atoms or sulfur atoms singly or in combination.

As a $C_{6-14}$ aryl group containing no hetero atoms, a phenyl group, a 1-indenyl group, a 2-indenyl group, a 3-indenyl group, a 4-indenyl group, a 5-indenyl group, a 6-indenyl group, a 7-indenyl group, an α-naphthyl group, a β-naphthyl group, a 1-tetrahydronaphthyl group, a 2-tetrahydronaphthyl group, a 5-tetrahydronaphthyl group, a 6-tetrahydronaphthyl group, an o-biphenylyl group, a β-biphenylyl group, a p-biphenylyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group or the like may be mentioned.

As a 5 to 7-membered $C_{2-6}$ heteromonocyclic group, a 2-thienyl group, a 3-thienyl group, a 2-furyl group, a 3-furyl group, a 2-pyranyl group, a 3-pyranyl group, a 4-pyranyl group, a 1-pyrrolyl group, a 2-pyrrolyl group, a 3-pyrrolyl group, a 1-imidazolyl group, a 2-imidazolyl group, a 4-imidazolyl group, a 1-pyrazolyl group, a 3-pyrazolyl group, a 4-pyrazolyl group, a 2-thiazolyl group, a 4-thiazolyl group, a 5-thiazolyl group, a 3-isothiazolyl group, a 4-isothiazolyl group, a 5-isothiazolyl group, a 2-oxazolyl group, a 4-oxazolyl group, a 5-oxazolyl group, a 3-isoxazolyl group, a 4-isoxazolyl group, a 5-isoxazolyl group, a 2-pyridyl group, a 3-pyridyl group, a 4-pyridyl group, a 2-pyrazinyl group, a 2-pyrimidinyl group, a 4-pyrimidinyl group, a 5-pyrimidinyl group, a 3-pyridazinyl group, a 4-pyridazinyl group, a 2-1,3,4-oxadiazolyl group, a 2-1,3,4-thiadiazolyl group, a 3-1,2,4-oxadiazolyl group, a 5-1,2,4-oxadiazolyl group, a 3-1,2,4-thiadiazolyl group, a 5-1,2,4-thiadiazolyl group, a 3-1,2,5-oxadiazolyl group, a 3-1,2,5-thiadiazolyl group or the like may be mentioned.

As a 8 to 10-membered $C_{5-9}$ fused heterocyclic group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 4-isobenzofuranyl group, a 5-isobenzofuranyl group, a 2-benzothienyl group, a 3-benzothienyl group, a 4-benzothienyl group, a 5-benzothienyl group, a 6-benzothienyl group, a 7-benzothienyl group, a 1-isobenzothienyl group, a 4-isobenzothienyl group, a 5-isobenzothienyl group, a 2-chromenyl group, a 3-chromenyl group, a 4-chromenyl group, a 5-chromenyl group, a 6-chromenyl group, a 7-chromenyl group, a 8-chromenyl group, a 1-indolizinyl group, a 2-indolizinyl group, a 3-indolizinyl group, a 5-indolizinyl group, a 6-indolizinyl group, a 7-indolizinyl group, a 8-indolizinyl group, a 1-isoindolyl group, a 2-isoindolyl group, a 4-isoindolyl group, a 5-isoindolyl group, a 1-indolyl group, a 2-indolyl group, a 3-indolyl group, a 4-indolyl group, a 5-indolyl group, a 6-indolyl group, a 7-indolyl group, 1-indazolyl group, a 2-indazolyl group, a 3-indazolyl group, a 4-indazolyl group, a 5-indazolyl group, a 6-indazolyl group, a 7-indazolyl group, a 1-purinyl group, a 2-purinyl group, a 3-purinyl group, a 6-purinyl group, a 7-purinyl group, a 8-purinyl group, a 2-quinolyl group, a 3-quinolyl group, a 4-quinolyl group, a 5-quinolyl group, a 6-quinolyl group, a 7-quinolyl group, a 8-quinolyl group, a 1-isoquinolyl group, a 3-isoquinolyl group, a 4-isoquinolyl group, a 5-isoquinolyl group, a 6-isoquinolyl group, a 7-isoquinolyl group, a 8-isoquinolyl group, a 1-phthalazinyl group, a 5-phthalazinyl group, a 6-phthalazinyl group, a 1-2,7-naphthyridinyl group, a 3-2,7-naphthyridinyl group, a 4-2,7-naphthyridinyl group, a 1-2,6-naphthyridinyl group, a 3-2,6-naphthyridinyl group, a 4-2,6-naphthyridinyl group, a 2-1,8-naphthyridinyl group, a 3-1,8-naphthyridinyl group, a 4-1,8-naphthyridinyl group, a 2-1,7-naphthyridinyl group, a 3-1,7-naphthyridinyl group, a 4-1,7-naphthyridinyl group, a 5-1,7-naphthyridinyl group, a 6-1,7-naphthyridinyl group, a 8-1,7-naphthyridinyl group, 2-1,6-naphthyridinyl group, a 3-1,6-naphthyridinyl group, a 4-1,6-naphthyridinyl group, a 5-1,6-naphthyridinyl group, a 7-1,6-naphthyridinyl group, a 8-1,6-naphthyridinyl group, a 2-1,5-naphthyridinyl group, a 3-1,5-naphthyridinyl group, a 4-1,5-naphthyridinyl group, a 6-1,5-naphthyridinyl group, a 7-1,5-naphthyridinyl group, a 8-1,5-naphthyridinyl group, a 2-quinoxalinyl group, a 5-quinoxalinyl group, a 6-quinoxalinyl group, a 2-quinazolinyl group, a 4-quinazolinyl group, a 5-quinazolinyl group, a 6-quinazolinyl group, a 7-quinazolinyl group, a 8-quinazolinyl group, a 3-cinnolinyl group, a 4-cinnolinyl group, a 5-cinnolinyl group, a 6-cinnolinyl group, a 7-cinnolinyl group, a 8-cinnolinyl group, a 2-pteridinyl group, a 4-pteridinyl group, a 6-pteridinyl group, a 7-pteridinyl group or the like may be mentioned.

A $C_{2-14}$ aryloxy group may be a $C_{6-14}$ aryloxy group containing no hetero atoms as ring constituting atoms or a $C_{2-9}$ aromatic heterocyclyloxy group, and a $C_{2-9}$ aromatic heterocyclyloxy group may be a 5 to 7-membered $C_{2-6}$ monocyclic heterocyclyloxy group or 8 to 10-membered $C_{5-9}$ fused bicyclic heterocyclyloxy group containing from 1 to 3 oxygen atoms, nitrogen atoms or sulfur atoms singly or in combination.

As a $C_{6-14}$ aryloxy group containing no hetero atoms, a phenyloxy group, a 1-indenyloxy group, a 2-indenyloxy group, a 3-indenyloxy group, a 4-indenyloxy group, a 5-indenyloxy group, a 6-indenyloxy group, a 7-indenyloxy group, an α-naphthyloxy group, a β-naphthyloxy group, a 1-tetrahydronaphthyloxy group, a 2-tetrahydronaphthyloxy group, a 5-tetrahydronaphthyloxy group, a 6-tetrahydronaphthyloxy group, an o-biphenylyloxy group, a m-biphenylyloxy group, a p-biphenylyloxy group, a 1-anthryloxy group, a 2-anthryloxy group, a 9-anthryloxy group, a 1-phenanthryloxy group, a 2-phenanthryloxy group, a 3-phenanthryloxy group, a 4-phenanthryloxy group, a 9-phenanthryloxy group or the like may be mentioned.

A 5 to 7-membered $C_{2-6}$ monocyclic heterocyclyloxy group may be a 2-thienyloxy group, a 3-thienyloxy group, a 2-furyloxy group, a 3-furyloxy group, a 2-pyranyloxy group, a 3-pyranyloxy group, a 4-pyranyloxy group, a 1-pyrrolyloxy group, a 2-pyrrolyloxy group, a 3-pyrrolyloxy group, a 1-imidazolyloxy group, a 2-imidazolyloxy group, a 4-imidazolyloxy group, a 1-pyrazolyloxy group, a 3-pyrazolyloxy group, a 4-pyrazolyloxy group, a 2-thiazolyloxy group, a 4-thiazolyloxy group, a 5-thiazolyloxy group, a 3-isothiazolyloxy group, a 4-isothiazolyloxy group, a 5-isothiazolyloxy group, a 2-oxazolyloxy group, a 4-oxazolyloxy group, a 5-oxazolyloxy group, a 3-isoxazolyloxy group, a 4-isoxazolyloxy group, a 5-isoxazolyloxy group, a 2-pyridyloxy group, a 3-pyridyloxy group, a 4-pyridyloxy group, a 2-pyrazinyloxy group, a 2-pyrimidinyloxy group, a 4-pyrimidinyloxy group, a 5-pyrimidinyloxy group, a 3-pyridazinyloxy group, a 4-pyridazinyloxy group, a 2-1,3,4-oxadiazolyloxy group, a 2-1,3,4-thiadiazolyloxy group, a 3-1,2,4-oxadiazolyloxy group, a 5-1,2,4-oxadiazolyloxy group, a 3-1,2,4-thiadiazolyloxy group, a 5-1,2,4-thiadiazolyloxy group, a 3-1,2,5-oxadiazolyloxy group, a 3-1,2,5-thiadiazolyloxy group or the like.

A 8 to 10-membered $C_{5-9}$ fused bicyclic heterocyclyloxy group may be a 2-benzofuranyloxy group, a 3-benzofuranyloxy group, a 4-benzofuranyloxy group, a 5-benzofuranyloxy group, a 6-benzofuranyloxy group, a 7-benzofuranyloxy group, a 1-isobenzofuranyloxy group, a 4-isobenzofuranyloxy group, a 5-isobenzofuranyloxy group, a 2-benzothienyloxy group, a 3-benzothienyloxy group, a 4-benzothienyloxy group, a 5-benzothienyloxy group, a 6-benzothienyloxy group, a 7-benzothienyloxy group, a 1-isobenzothienyloxy group, a 4-isobenzothienyloxy group, a 5-isobenzothienyloxy group, a 2-chromenyloxy group, a 3-chromenyloxy group, a 4-chromenyloxy group, a 5-chromenyloxy group, a 6-chromenyloxy group, a 7-chromenyloxy group, a 8-chromenyloxy group, a 1-indolizinyloxy group, a 2-indolizinyloxy group, a 3-indolizinyloxy group, a 5-indolizinyloxy group, a 6-indolizinyloxy group, a 7-indolizinyloxy group, a 8-indolizinyloxy group, a 1-isoindolyloxy group, a 2-isoindolyloxy group, a 4-isoindolyloxy group, a 5-isoindolyloxy group, a 1-indolyloxy group, a 2-indolyloxy group, a 3-indolyloxy group, a 4-indolyloxy group, a 5-indolyloxy group, a 6-indolyloxy group, a 7-indolyloxy group, 1-indazolyloxy group, a 2-indazolyloxy group, a 3-indazolyloxy group, a 4-indazolyloxy group, a 5-indazolyloxy group, a 6-indazolyloxy group, a 7-indazolyloxy group, a 1-purinyloxy group, a 2-purinyloxy group, a 3-purinyloxy group, a 6-purinyloxy group, a 7-purinyloxy group, a 8-purinyloxy group, a 2-quinolyloxy group, a 3-quinolyloxy group, a 4-quinolyloxy group, a 5-quinolyloxy group, a 6-quinolyloxy group, a 7-quinolyloxy group, a 8-quinolyloxy group, a 1-isoquinolyloxy group, a 3-isoquinolyloxy group, a 4-isoquinolyloxy group, a 5-isoquinolyloxy group, a 6-isoquinolyloxy group, a 7-isoquinolyloxy group, a 8-isoquinolyloxy group, a 1-phthalazinyloxy group, a 5-phthalazinyloxy group, a 6-phthalazinyloxy group, a 1-2,7-naphthyridinyloxy group, a 3-2,7-naphthyridinyloxy group, a 4-2,7-naphthyridinyloxy group, a 1-2,6-naphthyridinyloxy group, a 3-2,6-naphthyridinyloxy group, a 4-2,6-naphthyridinyloxy group, a 2-1,8-naphthyridinyloxy group, a 3-1,8-naphthyridinyloxy group, a 4-1,8-naphthyridinyloxy group, a 2-1,7-naphthyridinyloxy group, a 3-1,7-naphthyridinyloxy group, a 4-1,7-naphthyridinyloxy group, a 5-1,7-naphthyridinyloxy group, a 6-1,7-naphthyridinyloxy group, a 8-1,7-naphthyridinyloxy group, 2-1,6-naphthyridinyloxy group, a 3-1,6-naphthyridinyloxy group, a 4-1,6-naphthyridinyloxy group, a 5-1,6-naphthyridinyloxy group, a 7-1,6-naphthyridinyloxy group, a 8-1,6-naphthyridinyloxy group, a 2-1,5-naphthyridinyloxy group, a 3-1,5-naphthyridinyloxy group, a 4-1,5-naphthyridinyloxy group, a 6-1,5-naphthyridinyloxy group, a 7-1,5-naphthyridinyloxy group, a 8-1,5-naphthyridinyloxy group, a 2-quinoxalinyloxy group, a 5-quinoxalinyloxy group, a 6-quinoxalinyloxy group, a 2-quinazolinyloxy group, a 4-quinazolinyloxy group, a 5-quinazolinyloxy group, a 6-quinazolinyloxy group, a 7-quinazolinyloxy group, a 8-quinazolinyloxy group, a 3-cinnolinyloxy group, a 4-cinnolinyloxy group, a 5-cinnolinyloxy group, a 6-cinnolinyloxy group, a 7-cinnolinyloxy group, a 8-cinnolinyloxy group, a 2-pteridinyloxy group, a 4-pteridinyloxy group, a 6-pteridinyloxy group, a 7-pteridinyloxy group or the like.

A $C_{1-6}$ alkylcarbonyl group may linear, branched or a $C_{3-6}$ cycloalkylcarbonyl group, and methylcarbonyl, ethylcarbonyl, n-propylcarbonyl, i-propylcarbonyl, c-propylcarbonyl, n-butylcarbonyl, i-butylcarbonyl, s-butylcarbonyl, t-butylcarbonyl, c-butylcarbonyl, 1-methyl-c-propylcarbonyl, 2-methyl-c-propylcarbonyl, n-pentylcarbonyl, 1-methyl-n-butylcarbonyl, 2-methyl-n-butylcarbonyl, 3-methyl-n-butylcarbonyl, 1,1-dimethyl-n-propylcarbonyl, 1,2-dimethyl-n-propylcarbonyl, 2,2-dimethyl-n-propylcarbonyl, 1-ethyl-n-propylcarbonyl, c-pentylcarbonyl, 1-methyl-c-butylcarbonyl, 2-methyl-c-butylcarbonyl, 3-methyl-c-butylcarbonyl, 1,2-dimethyl-c-propylcarbonyl, 2,3-dimethyl-c-propylcarbonyl, 1-ethyl-c-propylcarbonyl, 2-ethyl-c-propylcarbonyl, n-hexylcarbonyl, 1-methyl-n-pentylcarbonyl, 2-methyl-n-pentylcarbonyl, 3-methyl-n-pentylcarbonyl, 4-methyl-n-pentylcarbonyl, 1,1-dimethyl-n-butylcarbonyl, 1,2-dimethyl-n-butylcarbonyl, 1,3-dimethyl-n-butylcarbonyl, 2,2-dimethyl-n-butylcarbonyl, 2,3-dimethyl-n-butylcarbonyl, 3,3-dimethyl-n-butylcarbonyl, 1-ethyl-n-butylcarbonyl, 2-ethyl-n-butylcarbonyl, 1,1,2-trimethyl-n-propylcarbonyl, 1,2,2-trimethyl-n-propylcarbonyl, 1-ethyl-1-methyl-n-propylcarbonyl, 1-ethyl-2-methyl-n-propylcarbonyl, c-hexylcarbonyl, 1-methyl-c-pentylcarbonyl, 2-methyl-c-pentylcarbonyl, 3-methyl-c-pentylcarbonyl, 1-ethyl-c-butylcarbonyl, 2-ethyl-c-butylcarbonyl, 3-ethyl-c-butylcarbonyl, 1,2-dimethyl-c-butylcarbonyl, 1,3-dimethyl-c-butylcarbonyl, 2,2-dimethyl-c-butylcarbonyl, 2,3-dimethyl-c-butylcarbonyl, 2,4-dimethyl-c-butylcarbonyl, 3,3-dimethyl-c-butylcarbonyl, 1-n-propyl-c-propylcarbonyl, 2-n-propyl-c-propylcarbonyl, 1-i-propyl-c-propylcarbonyl, 2-i-propyl-c-propylcarbonyl, 1,2,2-trimethyl-c-propylcarbonyl, 1,2,3-trimethyl-c-propylcarbonyl, 2,2,3-trimethyl-c-propylcarbonyl, 1-ethyl-2-methyl-c-propylcarbonyl, 2-ethyl-1-methyl-c-propylcarbonyl, 2-ethyl-2-methyl-c-propylcarbonyl, 2-ethyl-3-methyl-c-propylcarbonyl or the like may be mentioned.

A $C_{1-10}$ alkylcarbonyl group may linear, branched or a $C_{3-10}$ cycloalkylcarbonyl group, and as specific examples, in addition to those mentioned above, 1-methyl-1-ethyl-n-pentylcarbonyl, 1-heptylcarbonyl, 2-heptylcarbonyl, 1-ethyl-1,2-dimethyl-n-propylcarbonyl, 1-ethyl-2,2-dimethyl-n-propylcarbonyl, 1-octylcarbonyl, 3-octylcarbonyl, 4-methyl-3-n-heptylcarbonyl, 6-methyl-2-n-heptylcarbonyl, 2-propyl-1-n-heptylcarbonyl, 2,4,4-trimethyl-1-n-pentylcarbonyl, 1-nonylcarbonyl, 2-nonylcarbonyl, 2,6-dimethyl-4-n-heptylcarbonyl, 3-ethyl-2,2-dimethyl-3-n-pentylcarbonyl, 3,5,5-trimethyl-1-n-hexylcarbonyl, 1-decylcarbonyl, 2-decylcarbonyl, 4-decylcarbonyl, 3,7-dimethyl-1-n-octylcarbonyl, 3,7-dimethyl-3-n-octylcarbonyl or the like may be mentioned.

A $C_{1-3}$ alkoxy group may be linear, branched or a $C_3$ cycloalkoxy group, and methoxy, ethoxy, n-propoxy, i-propoxy, c-propoxy or the like may be mentioned.

A $C_{1-6}$ alkoxy group may be linear, branched or a $C_{3-6}$ cycloalkoxy group, and as specific examples, in addition to those mentioned above, n-butoxy, i-butoxy, s-butoxy, t-butoxy, c-butoxy, 1-methyl-c-propoxy, 2-methyl-c-propoxy, n-pentyloxy, 1-methyl-n-butoxy, 2-methyl-n-butoxy, 3-methyl-n-butoxy, 1,1-dimethyl-n-propoxy, 1,2-dimethyl-n-propoxy, 2,2-dimethyl-n-propoxy, 1-ethyl-n-propoxy, c-pentyloxy, 1-methyl-c-butoxy, 2-methyl-c-butoxy, 3-methyl-c-butoxy, 1,2-dimethyl-c-propoxy, 2,3-dimethyl-c-propoxy, 1-ethyl-c-propoxy, 2-ethyl-c-propoxy, n-hexyloxy, 1-methyl-n-pentyloxy, 2-methyl-n-pentyloxy, 3-methyl-n-pentyloxy, 4-methyl-n-pentyloxy, 1,1-dimethyl-n-butoxy, 1,2-dimethyl-n-butoxy, 1,3-dimethyl-n-butoxy, 2,2-dimethyl-n-butoxy, 2,3-dimethyl-n-butoxy, 3,3-dimethyl-n-butoxy, 1-ethyl-n-butoxy, 2-ethyl-n-butoxy, 1,1,2-trimethyl-n-propoxy, 1,2,2-trimethyl-n-propoxy, 1-ethyl-1-methyl-n-propoxy, 1-ethyl-2-methyl-n-propoxy, c-hexyloxy, 1-methyl-c-pentyloxy, 2-methyl-c-pentyloxy, 3-methyl-c-pentyloxy, 1-ethyl-c-butoxy, 2-ethyl-c-butoxy, 3-ethyl-c-butoxy, 1,2-dimethyl-c-butoxy, 1,3-dimethyl-c-butoxy, 2,2-dimethyl-c-butoxy, 2,3-dimethyl-c-butoxy, 2,4-dimethyl-c-butoxy, 3,3-dimethyl-c-butoxy, 1-n-propyl-c-propoxy, 2-n-propyl-c-propoxy, 1-i-propyl-c-propoxy, 2-i-propyl-c-propoxy, 1,2,2-trimethyl-c-propoxy, 1,2,3-trimethyl-c-propoxy, 2,2,3-trimethyl-c-propoxy, 1-ethyl-2-methyl-c-propoxy, 2-ethyl-1-methyl-c-propoxy, 2-ethyl-2-methyl-c-propoxy, 2-ethyl-3-methyl-c-propoxy or the like may be mentioned.

A $C_{1-10}$ alkoxy group may be linear, branched or a $C_{3-10}$ cycloalkoxy group, and as specific examples, in addition to those mentioned above, 1-methyl-1-ethyl-n-pentyloxy, 1-heptyloxy, 2-heptyloxy, 1-ethyl-1,2-dimethyl-n-propyloxy, 1-ethyl-2,2-dimethyl-n-propyloxy, 1-octyloxy, 3-octyloxy, 4-methyl-3-n-heptyloxy, 6-methyl-2-n-heptyloxy, 2-propyl-1-n-heptyloxy, 2,4,4-trimethyl-1-n-pentyloxy, 1-nonyloxy, 2-nonyloxy, 2,6-dimethyl-4-n-heptyloxy, 3-ethyl-2,2-dimethyl-3-n-pentyloxy, 3,5,5-trimethyl-1-n-hexyloxy, 1-decyloxy, 2-decyloxy, 4-decyloxy, 3,7-dimethyl-1-n-octyloxy, 3,7-dimethyl-3-n-octyloxy or the like may be mentioned.

A $C_{1-6}$ alkoxycarbonyl group may be linear, branched or a $C_{3-6}$ cycloalkoxycarbonyl group, and methoxycarbonyl, ethoxycarbonyl, n-propoxycarbonyl, i-propoxycarbonyl, c-propoxycarbonyl, n-butoxycarbonyl, i-butoxycarbonyl, s-butoxycarbonyl, t-butoxycarbonyl, c-butoxycarbonyl, 1-methyl-c-propoxycarbonyl, 2-methyl-c-propoxycarbonyl, n-pentyloxycarbonyl, 1-methyl-n-butoxycarbonyl, 2-methyl-n-butoxycarbonyl, 3-methyl-n-butoxycarbonyl, 1,1-dimethyl-n-propoxycarbonyl, 1,2-dimethyl-n-propoxycarbonyl, 2,2-dimethyl-n-propoxycarbonyl, 1-ethyl-n-propoxycarbonyl, c-pentyloxycarbonyl, 1-methyl-c-butoxycarbonyl, 2-methyl-c-butoxycarbonyl, 3-methyl-c-butoxycarbonyl, 1,2-dimethyl-c-propoxycarbonyl, 2,3-dimethyl-c-propoxycarbonyl, 1-ethyl-c-propoxycarbonyl, 2-ethyl-c-propoxycarbonyl, n-hexyloxycarbonyl, 1-methyl-n-pentyloxycarbonyl, 2-methyl-n-pentyloxycarbonyl, 3-methyl-n-pentyloxycarbonyl, 4-methyl-n-pentyloxycarbonyl, 1,1-dimethyl-n-butoxycarbonyl, 1,2-dimethyl-n-butoxycarbonyl, 1,3-dimethyl-n-butoxycarbonyl, 2,2-dimethyl-n-butoxycarbonyl, 2,3-dimethyl-n-butoxycarbonyl, 3,3-dimethyl-n-butoxycarbonyl, 1-ethyl-n-butoxycarbonyl, 2-ethyl-n-butoxycarbonyl, 1,1,2-trimethyl-n-propoxycarbonyl, 1,2,2-trimethyl-n-propoxycarbonyl, 1-ethyl-1-methyl-n-propoxycarbonyl, 1-ethyl-2-methyl-n-propoxycarbonyl, c-hexyloxycarbonyl, 1-methyl-c-pentyloxycarbonyl, 2-methyl-c-pentyloxycarbonyl, 3-methyl-c-pentyloxycarbonyl, 1-ethyl-c-butoxycarbonyl, 2-ethyl-c-butoxycarbonyl, 3-ethyl-c-butoxycarbonyl, 1,2-dimethyl-c-butoxycarbonyl, 1,3-dimethyl-c-butoxycarbonyl, 2,2-dimethyl-c-butoxycarbonyl, 2,3-dimethyl-c-butoxycarbonyl, 2,4-dimethyl-c-butoxycarbonyl, 3,3-dimethyl-c-butoxycarbonyl, 1-n-propyl-c-propoxycarbonyl, 2-n-propyl-c-propoxycarbonyl, 1-i-propyl-c-propoxycarbonyl, 2-i-propyl-c-propoxycarbonyl, 1,2,2-trimethyl-c-propoxycarbonyl, 1,2,3-trimethyl-c-propoxycarbonyl, 2,2,3-trimethyl-c-propoxycarbonyl, 1-ethyl-2-methyl-c-propoxycarbonyl, 2-ethyl-1-methyl-c-propoxycarbonyl, 2-ethyl-2-methyl-c-propoxycarbonyl, 2-ethyl-3-methyl-c-propoxycarbonyl or the like may be mentioned.

A $C_{1-10}$ alkoxycarbonyl group may be linear, branched or a $C_{3-10}$ cycloalkoxycarbonyl group, and as specific examples, in addition to those mentioned above, 1-methyl-1-ethyl-n-pentyloxycarbonyl, 1-heptyloxycarbonyl, 2-heptyloxycarbonyl, 1-ethyl-1,2-dimethyl-n-propyloxycarbonyl, 1-ethyl-2,2-dimethyl-n-propyloxycarbonyl, 1-octyloxycarbonyl, 3-octyloxycarbonyl, 4-methyl-3-n-heptyloxycarbonyl, 6-methyl-2-n-heptyloxycarbonyl, 2-propyl-1-n-heptyloxycarbonyl, 2,4,4-trimethyl-1-n-pentyloxycarbonyl, 1-nonyloxycarbonyl, 2-nonyloxycarbonyl, 2,6-dimethyl-4-n-heptyloxycarbonyl, 3-ethyl-2,2-dimethyl-3-n-pentyloxycarbonyl, 3,5,5-trimethyl-1-n-hexyloxycarbonyl, 1-decyloxycarbonyl, 2-decyloxycarbonyl, 4-decyloxycarbonyl, 3,7-dimethyl-1-n-octyloxycarbonyl, 3,7-dimethyl-3-n-octyloxycarbonyl or the like may be mentioned.

A $C_{1-10}$ alkylcarbonyloxy group may be linear, branched or a $C_{3-10}$ cycloalkylcarbonyloxy group, and methylcarbonyloxy, ethylcarbonyloxy, n-propylcarbonyloxy, i-propylcarbonyloxy, c-propylcarbonyloxy, n-butylcarbonyloxy, i-butylcarbonyloxy, s-butylcarbonyloxy, t-butylcarbonyloxy, c-butylcarbonyloxy, 1-methyl-c-propylcarbonyloxy, 2-methyl-c-propylcarbonyloxy, n-pentylcarbonyloxy, 1-methyl-n-butylcarbonyloxy, 2-methyl-n-butylcarbonyloxy, 3-methyl-n-butylcarbonyloxy, 1,1-dimethyl-n-propylcarbonyloxy, 1,2-dimethyl-n-propylcarbonyloxy, 2,2-dimethyl-n-propylcarbonyloxy, 1-ethyl-n-propylcarbonyloxy, c-pentylcarbonyloxy, 1-methyl-c-butylcarbonyloxy, 2-methyl-c-butylcarbonyloxy, 3-methyl-c-butylcarbonyloxy, 1,2-dimethyl-c-propylcarbonyloxy, 2,3-dimethyl-c-propylcarbonyloxy, 1-ethyl-c-propylcarbonyloxy, 2-ethyl-c-propylcarbonyloxy, n-hexylcarbonyloxy, 1-methyl-n-pentylcarbonyloxy, 2-methyl-n-pentylcarbonyloxy, 3-methyl-n-pentylcarbonyloxy, 4-methyl-n-pentylcarbonyloxy, 1,1-dimethyl-n-butylcarbonyloxy, 1,2-dimethyl-n-butylcarbonyloxy, 1,3-dimethyl-n-butylcarbonyloxy, 2,2-dimethyl-n-butylcarbonyloxy, 2,3-dimethyl-n-butylcarbonyloxy, 3,3-dimethyl-n-butylcarbonyloxy, 1-ethyl-n-butylcarbonyloxy, 2-ethyl-n-butylcarbonyloxy, 1,1,2-trimethyl-n-propylcarbonyloxy, 1,2,2-trimethyl-n-propylcarbonyloxy, 1-ethyl-1-methyl-n-propylcarbonyloxy, 1-ethyl-2-methyl-n-propylcarbonyloxy, c-hexylcarbonyloxy, 1-methyl-c-pentylcarbonyloxy, 2-methyl-c-pentylcarbonyloxy, 3-methyl-c-pentylcarbonyloxy, 1-ethyl-c-butylcarbonyloxy, 2-ethyl-c-butylcarbonyloxy, 3-ethyl-c-butylcarbonyloxy, 1,2-dimethyl-c-butylcarbonyloxy, 1,3-dimethyl-c-butylcarbonyloxy, 2,2-dimethyl-c-butylcarbonyloxy, 2,3-dimethyl-c-butylcarbonyloxy, 2,4-dimethyl-c-butylcarbonyloxy, 3,3-dimethyl-c-butylcarbonyloxy, 1-n-propyl-c-propylcarbonyloxy, 2-n-propyl-c-propylcarbonyloxy, 1-i-propyl-c-propylcarbonyloxy, 2-i-propyl-c-propylcarbonyloxy, 1,2,3-trimethyl-c-propylcarbonyloxy, 1,2,2-trimethyl-c-propylcarbonyloxy, 2,2,3-trimethyl-c-propylcarbonyloxy, 1-ethyl-2-methyl-c-propylcarbonyloxy, 2-ethyl-1-methyl-c-propylcarbonyloxy, 2-ethyl-2-methyl-c-propylcarbonyloxy, 2-ethyl-3-methyl-c-propylcarbonyloxy, 1-methyl-1-ethyl-n-pentylcarbonyloxy, 1-heptylcarbonyloxy, 2-heptylcarbonyloxy, 1-ethyl-1,2-dimethyl-n-propylcarbonyloxy, 1-ethyl-2,2-dimethyl-n-propylcarbonyloxy, 1-octylcarbonyloxy, 3-octylcarbonyloxy, 4-methyl-3-n-heptylcarbonyloxy, 6-methyl-2-n-heptylcarbonyloxy, 2-propyl-1-n-heptylcarbonyloxy, 2,4,4-trimethyl-1-n-pentylcarbonyloxy, 1-nonylcarbonyloxy, 2-nonylcarbonyloxy, 2,6-dimethyl-4-n-heptylcarbonyloxy, 3-ethyl-2,2-dimethyl-3-n-pentylcarbonyloxy, 3,5,5-trimethyl-1-n-hexylcarbonyloxy, 1-decylcarbonyloxy, 2-decylcarbonyloxy, 4-decylcarbonyloxy, 3,7-dimethyl-1-n-octylcarbonyloxy, 3,7-dimethyl-3-n-octylcarbonyloxy or the like may be mentioned.

A $C_{1-10}$ alkylcarbonylamino group may be linear, branched or a $C_{3-10}$ cycloalkylcarbonylamino group, and methylcarbonylamino, ethylcarbonylamino, n-propylcarbonylamino, i-propylcarbonylamino, c-propylcarbonylamino, n-butylcarbonylamino, i-butylcarbonylamino, s-butylcarbonylamino, t-butylcarbonylamino, c-butylcarbonylamino, 1-methyl-c-propylcarbonylamino, 2-methyl-c-propylcarbonylamino, n-pentylcarbonylamino, 1-methyl-n-butylcarbonylamino, 2-methyl-n-butylcarbonylamino, 3-methyl-n-butylcarbonylamino, 1,1-dimethyl-n-propylcarbonylamino, 1,2-dimethyl-n-propylcarbonylamino, 2,2-dimethyl-n-propylcarbonylamino, 1-ethyl-n-propylcarbonylamino, c-pentylcarbonylamino, 1-methyl-c-butylcarbonylamino, 2-methyl-c-butylcarbonylamino, 3-methyl-c-butylcarbonylamino, 1,2-dimethyl-c-propylcarbonylamino, 2,3-dimethyl-c-propylcarbonylamino, 1-ethyl-c-propylcarbonylamino, 2-ethyl-c-propylcarbonylamino, n-hexylcarbonylamino, 1-methyl-n-pentylcarbonylamino, 2-methyl-n-pentylcarbonylamino, 3-methyl-n-pentylcarbonylamino, 4-methyl-n-pentylcarbonylamino, 1,1-dimethyl-n-butylcarbonylamino, 1,2-dimethyl-n-butylcarbonylamino, 1,3-dimethyl-n-butylcarbonylamino, 2,2-dimethyl-n-butylcarbonylamino, 2,3-dimethyl-n-butylcarbonylamino, 3,3-dimethyl-n-butylcarbonylamino, 1-ethyl-n-butylcarbonylamino, 2-ethyl-n-butylcarbonylamino, 1,1,2-trimethyl-n-propylcarbonylamino, 1,2,2-trimethyl-n-propylcarbonylamino, 1-ethyl-1-methyl-n-propylcarbonylamino, 1-ethyl-2-methyl-n-propylcarbonylamino, c-hexylcarbonylamino, 1-methyl-c-pentylcarbonylamino, 2-methyl-c-pentylcarbonylamino, 3-methyl-c-pentylcarbonylamino, 1-ethyl-c-butylcarbonylamino, 2-ethyl-c-butylcarbonylamino, 3-ethyl-c-butylcarbonylamino, 1,2-dimethyl-c-butylcarbonylamino, 1,3-dimethyl-c-butylcarbonylamino, 2,2-dimethyl-c-butylcarbonylamino, 2,3-dimethyl-c-butylcarbonylamino, 2,4-dimethyl-c-butylcarbonylamino, 3,3-dimethyl-c-butylcarbonylamino, 1-n-propyl-c-propylcarbonylamino, 2-n-propyl-c-propylcarbonylamino, 1-i-propyl-c-propylcarbonylamino, 2-i-propyl-c-propylcarbonylamino, 1,2,2-trimethyl-c-propyl-carbonylamino, 1,2,3-trimethyl-c-propylcarbonylamino, 2,2,3-trimethyl-c-propylcarbonylamino, 1-ethyl-2-methyl-c-propylcarbonylamino, 2-ethyl-1-methyl-c-propylcarbonylamino, 2-ethyl-2-methyl-c-propylcarbonylamino, 2-ethyl-3-methyl-c-propylcarbonylamino, 1-methyl-1-ethyl-n-pentylcarbonylamino, 1-heptylcarbonylamino, 2-heptylcarbonylamino, 1-ethyl-1,2-dimethyl-n-propylcarbonylamino, 1-ethyl-2,2-dimethyl-n-propylcarbonylamino, 1-octylcarbonylamino, 3-octylcarbonylamino, 4-methyl-3-n-heptylcarbonylamino, 6-methyl-2-n-heptylcarbonylamino, 2-propyl-1-n-heptylcarbonylamino, 2,4,4-trimethyl-1-n-pentylcarbonylamino, 1-nonylcarbonylamino, 2-nonylcarbonylamino, 2,6-dimethyl-4-n-heptylcarbonylamino, 3-ethyl-2,2-dimethyl-3-n-pentylcarbonylamino, 3,5,5-trimethyl-1-n-hexylcarbonylamino, 1-decylcarbonylamino, 2-decylcarbonylamino, 4-decylcarbonylamino, 3,7-dimethyl-1-n-octylcarbonylamino, 3,7-dimethyl-3-n-octylcarbonylamino or the like may be mentioned.

A $C_{1-10}$ monoalkylamino group may be linear, branched or a $C_{3-10}$ cycloalkylamino group, and methylamino, ethylamino, n-propylamino, i-propylamino, c-propylamino, n-butylamino, i-butylamino, s-butylamino, t-butylamino, c-butylamino, 1-methyl-c-propylamino, 2-methyl-c-propylamino, n-pentylamino, 1-methyl-n-butylamino, 2-methyl-n-butylamino, 3-methyl-n-butylamino, 1,1-dimethyl-n-propylamino, 1,2-dimethyl-n-propylamino, 2,2-dimethyl-n-propylamino, 1-ethyl-n-propylamino, c-pentylamino, 1-methyl-c-butylamino, 2-methyl-c-butylamino, 3-methyl-c-butylamino, 1,2-dimethyl-c-propylamino, 2,3-dimethyl-c-propylamino, 1-ethyl-c-propylamino, 2-ethyl-c-propylamino, n-hexylamino, 1-methyl-n-pentylamino, 2-methyl-n-pentylamino, 3-methyl-n-pentylamino, 4-methyl-n- pentylamino, 1,1-dimethyl-n-butylamino, 1,2-dimethyl-n-butylamino, 1,3-dimethyl-n-butylamino, 2,2-dimethyl-n-butylamino, 2,3-dimethyl-n-butylamino, 3,3-dimethyl-n-butylamino, 1-ethyl-n-butylamino, 2-ethyl-n-butylamino, 1,1,2-trimethyl-n-propylamino, 1,2,2-trimethyl-n-propylamino, 1-ethyl-1-methyl-n-propylamino, 1-ethyl-2-methyl-n-propylamino, c-hexylamino, 1-methyl-c-pentylamino, 2-methyl-c-pentylamino, 3-methyl-c-pentylamino, 1-ethyl-c-butylamino, 2-ethyl-c-butylamino, 3-ethyl-c-butylamino, 1,2-dimethyl-c-butylamino, 1,3-dimethyl-c-butylamino, 2,2-dimethyl-c-butylamino, 2,3-dimethyl-c-butylamino, 2,4-dimethyl-c-butylamino, 3,3-dimethyl-c-butylamino, 1-n-propyl-c-propylamino, 2-n-propyl-c-propylamino, 1-i-propyl-c-propylamino, 2-i-propyl-c-propylamino, 1,2,2-trimethyl-c-propylamino, 1,2,3-trimethyl-c-propylamino, 2,2,3-trimethyl-c-propylamino, 1-ethyl-2-methyl-c-propylamino, 2-ethyl-1-methyl-c-propylamino, 2-ethyl-2-methyl-c-propylamino, 2-ethyl-3-methyl-c-propylamino, 1-methyl-1-ethyl-n-pentylamino, 1-heptylamino, 2-heptylamino, 1-ethyl-1,2-dimethyl-n-propylamino, 1-ethyl-2,2-dimethyl-n-propylamino, 1-octylamino, 3-octylamino, 4-methyl-3-n-heptylamino, 6-methyl-2-n-heptylamino, 2-propyl-1-n-heptylamino, 2,4,4-trimethyl-1-n-pentylamino, 1-nonylamino, 2-nonylamino, 2,6-dimethyl-4-n-heptylamino, 3-ethyl-2,2-dimethyl-3-n-pentylamino, 3,5,5-trimethyl-1-n-hexylamino, 1-decylamino, 2-decylamino, 4-decylamino, 3,7-dimethyl-1-n-octylamino, 3,7-dimethyl-3-n-octylamino or the like may be mentioned.

A di-$C_{1-10}$ alkylamino group may be symmetric or asymmetric. A symmetric di-$C_{1-10}$ alkylamino group may be linear, branched or a $C_{3-10}$ cycloalkylamino group, and dimethylamino, diethylamino, di-n-propylamino, di-i-propylamino, di-c-propylamino, di-n-butylamino, di-i-butylamino, di-s-butylamino, di-t-butylamino, di-c-butylamino, di-(1-methyl-c-propyl)amino, di-(2-methyl-c-propyl)amino, di-n-pentylamino, di-(1-methyl-n-butyl)amino, di-(2-methyl-n-butyl)amino, di-(3-methyl-n-butyl)amino, di-(1,1-dimethyl-n-propyl)amino, di-(1,2-dimethyl-n-propyl)amino, di-(2,2-dimethyl-n-propyl)amino, di-(1-ethyl-n-propyl)amino, di-c-pentylamino, di-(1-methyl-c-butyl)amino, di-(2-methyl-c-butyl)amino, di-(3-methyl-c-butyl)amino, di-(1,2-dimethyl-c-propyl)amino, di-(2,3-dimethyl-c-propyl)amino, di-(1-ethyl-c-propyl)amino, di-(2-ethyl-c-propyl)amino, di-n-hexylamino, di-(1-methyl-n-pentyl)amino, di-(2-methyl-n-pentyl)amino, di-(3-methyl-n-pentyl)amino, di-(4-methyl-n-pentyl)amino, di-(1,1-dimethyl-n-butyl)amino, di-(1,2-dimethyl-n-butyl)amino, di-(1,3-dimethyl-n-butyl)amino, di-(2,2-dimethyl-n-butyl)amino, di-(2,3-dimethyl-n-butyl)amino, di-(3,3-dimethyl-n-butyl)amino, di-(1-ethyl-n-butyl)amino, di-(2-ethyl-n-butyl)amino, di-(1,1,2-trimethyl-n-propyl)amino, di-(1,2,2-trimethyl-n-propyl)amino, di-(1-ethyl-1-methyl-n-propyl)amino, di-(1-ethyl-2-methyl-n-propyl)amino, di-c-hexylamino, di-(1-methyl-c-pentyl)amino, di-(2-methyl-c-pentyl)amino, di-(3-methyl-c-pentyl)amino, di-(1-ethyl-c-butyl)amino, di-(2-ethyl-c-butyl)amino, di-(3-ethyl-c-butyl)amino, di-(1,2-dimethyl-c-butyl)amino, di-(1,3-dimethyl-c-butyl)amino, di-(2,2-dimethyl-c-butyl)amino, di-(2,3-dimethyl-c-butyl)amino, di-(2,4-dimethyl-c-butyl)amino, di-(3,3-dimethyl-c-butyl)amino, di-(1-n-propyl-c-propyl)amino, di-(2-n-propyl-c-propyl)amino, di-(1-i-propyl-c-propyl)amino, di-(2-i-propyl-c-propyl)amino, di-(1,2,2-trimethyl-c-propyl)amino, di-(1,2,3-trimethyl-c-propyl)amino, di-(2,2,3-trimethyl-c-propyl)amino, di-(1-ethyl-2-methyl-c-propyl)amino, di-(2-ethyl-1-methyl-c-propyl)amino, di-(2-ethyl-2-methyl-c-propyl)amino, di-(2-ethyl-3-methyl-c-propyl)amino, di-(1-methyl-1-ethyl-n-pentyl)amino, di-(1-heptyl)amino, di-(2-heptyl)amino, di-(1-ethyl-1,2-dimethyl-n-propyl)amino, di-(1-ethyl-2,2-dimethyl-n-propyl)amino, di-(1-octyl)amino, di-(3-octyl)amino, di-(4-methyl-3-n-heptyl)amino, di-(6-methyl-2-n-heptyl)amino, di-(2-propyl-1-n-heptyl)amino, di-(2,4,4-trimethyl-1-n-pentyl)amino, di-(1-nonyl)amino, di-(2-nonyl)amino, di-(2,6-dimethyl-4-n-heptyl)amino, di-(3-ethyl-2,2-dimethyl-3-n-pentyl)amino, di-(3,5,5-trimethyl-1-n-hexyl)amino, di-(1-decyl)amino, di-(2-decyl)amino, di-(4-decyl)amino, di-(3,7-dimethyl-1-n-octyl)amino, di-(3,7-dimethyl-3-n-octyl)amino or the like may be mentioned.

An asymmetric di-$C_{1-10}$ alkylamino group may be linear, branched or a $C_{3-10}$ cycloalkylamino group, and (methyl, ethyl)amino, (methyl, n-propyl)amino, (methyl, i-propyl)amino, (methyl, c-propyl)amino, (methyl, n-butyl)amino, (methyl, i-butyl)amino, (methyl, s-butyl)amino, (methyl, t-butyl)amino, (methyl, n-pentyl)amino, (methyl, c-pentyl)amino, (methyl, n-hexyl)amino, (methyl, c-hexyl)amino, (ethyl, n-propyl)amino, (ethyl, i-propyl)amino, (ethyl, c-propyl)amino, (ethyl, n-butyl)amino, (ethyl, i-butyl)amino, (ethyl, s-butyl)amino, (ethyl, t-butyl)amino, (ethyl, n-pentyl)amino, (ethyl, c-pentyl)amino, (ethyl, n-hexyl)amino, (ethyl, c-hexyl)amino, (n-propyl, i-propyl)amino, (n-propyl, c-propyl)amino, (n-propyl, n-butyl)amino, (n-propyl, i-butyl)amino, (n-propyl, s-butyl)amino, (n-propyl, t-butyl)amino, (n-propyl, n-pentyl)amino, (n-propyl, c-pentyl)amino, (n-propyl, n-hexyl)amino, (n-propyl, c-hexyl)amino, (i-propyl, c-propyl)amino, (i-propyl, n-butyl)amino, (i-propyl, i-butyl)amino, (i-propyl, s-butyl)amino, (i-propyl, t-butyl)amino, (i-propyl, n-pentyl)amino, (i-propyl, c-pentyl)amino, (i-propyl, n-hexyl)amino, (i-propyl, c-hexyl)amino, (c-propyl, n-butyl)amino, (c-propyl, i-butyl)amino, (c-propyl, s-butyl)amino, (c-propyl, t-butyl)amino, (c-propyl, n-pentyl)amino, (c-propyl, c-pentyl)amino, (c-propyl, n-hexyl)amino, (c-propyl, c-hexyl)amino, (n-butyl, i-butyl)amino, (n-butyl, s-butyl)amino, (n-butyl, t-butyl)amino, (n-butyl, n-pentyl)amino, (n-butyl, c-pentyl)amino, (n-butyl, n-hexyl)amino, (n-butyl, c-hexyl)amino, (i-butyl, s-butyl)amino, (i-butyl, t-butyl)amino, (i-butyl, n-pentyl)amino, (i-butyl, c-pentyl)amino, (i-butyl, n-hexyl)amino, (i-butyl, c-hexyl)amino, (s-butyl, t-butyl)amino, (s-butyl, n-pentyl)amino, (s-butyl, c-pentyl)amino, (s-butyl, n-hexyl)amino, (s-butyl, c-hexyl)amino, (t-butyl, n-pentyl)amino, (t-butyl, c-pentyl)amino, (t-butyl, n-hexyl)amino, (t-butyl, c-hexyl)amino, (n-pentyl, c-pentyl)amino, (n-pentyl, n-hexyl)amino, (n-pentyl, c-hexyl)amino, (c-pentyl, n-hexyl)amino, (c-pentyl, c-hexyl)amino, (n-hexyl, c-hexyl)amino, (methyl, n-heptyl)amino, (methyl, n-octyl)amino, (methyl, n-nonanyl)amino, (methyl, n-decyl)amino, (ethyl, n-heptyl)amino, (ethyl, n-octyl)amino, (ethyl, n-nonanyl)amino, (ethyl, n-decyl)amino or the like may be mentioned.

The protecting group in a protected hydroxyl group may be a $C_{1-4}$ alkoxymethyl group (such as MOM: methoxymethyl, MEM: 2-methoxyethoxymethyl, ethoxymethyl, n-propoxymethyl, i-propoxymethyl, n-butoxymethyl, iBM: isobutyloxymethyl, BUM: t-butoxymethyl, POM: pivaloyloxymethyl, SEM: trimethylsilylethoxymethyl and the like, preferably a $C_{1-2}$ alkoxymethyl or the like), an aryloxymethyl (such as BOM: benzyloxymethyl, PMBM: p-methoxybenzyloxymethyl, P-AOM: p-anisyloxymethyl and the like, preferably benzyloxymethyl), a alkylaminomethyl group (such as dimethylaminomethyl), a substituted acetamidomethyl group (such as Acm: acetamidomethyl, Tacm: trimethylacetamidomethyl and the like), a substituted thiomethyl group (such as MTM: methylthiomethyl, PTM: phenylthiomethyl, Btm: benzylthiomethyl and the like), a carboxyl group, a $C_{1-7}$ acyl group (such as formyl, acetyl, fluoroacetyl, difluoroacetyl, trifluoroacetyl, chloroacetyl, dichloroacetyl, trichloroacetyl, propionyl, Pv: pivaloyl, tigloyl and the like), an arylcarbonyl group (such as benzoyl, p-bromobenzoyl, p-nitrobenzoyl, 2,4-dinitrobenzoyl, benzoylformyl, benzoylpropionyl, phenylpropionyl and the like), a $C_{1-4}$ alkoxycarbonyl group (such as methoxycarbonyl, ethoxycarbonyl, n-propoxycarbonyl, i-propoxycarbonyl, n-butoxycarbonyl, i-butoxycarbonyl, BOC: t-butoxycarbonyl, AOC: t-amyloxycarbonyl, VOC: vinyloxycarbonyl, AOC: allyloxycarbonyl, Teoc: 2-(trimethylsilyl)ethoxycarbonyl, Troc: 2,2,2-trichloroethoxycarbonyl and the like, preferably BOC and the like), an aryloxycarbonyl group (such as Z: benzyloxycarbonyl, p-nitrobenzyloxycarbonyl, MOZ: p-methoxybenzyloxycarbonyl and the like), a $C_{1-4}$ alkylaminocarbonyl group (such as methylcarbamoyl, Ec: ethylcarbamoyl, n-propylcarbamoyl and the like), an arylaminocarbonyl group (such as phenylcarbamoyl and the like), a trialkylsilyl group (such as TMS: trimethylsilyl, TES: triethylsilyl, TIPS: triisopropylsilyl, DEIPS: diethylisopropylsilyl, DMIPS: dimethylisopropylsilyl, DTBMS: di-t-butylmethylsilyl, IPDMS: isopropyldimethylsilyl, TBDMS: t-butyldimethylsilyl, TDS: thexyldimethylsilyl and the like, preferably t-butyldimethylsilyl and the like), a trialkylarylsilyl group (such as DPMS: diphenylmethylsilyl, TBDPS: t-butyldiphenylsilyl, TBMPS: t-butyldimethoxyphenylsilyl, TPS: triphenylsilyl and the like), an alkylsulfonyl group, (such as Ms: methanesulfonyl, ethanesulfonyl and the like) or an arylsulfonyl group (such as benzenesulfonyl, Ts: p-toluenesulfonyl, p-chlorobenzenesulfonyl, MBS: p-methoxybenzenesulfonyl, m-nitrobenzenesulfonyl, o-nitrobenzenesulfonyl, p-nitrobenzenesulfonyl, 2,4-nitrobenzenesulfonyl, iMds: 2,6-dimethoxy-4-methylbenzenesulfonyl, Mds: 2,6-dimethyl-4-methoxybenzenesulfonyl, Mtb: 2,4,6-trimethoxybenzenesulfonyl, Mte: 2,3,5,6-tetramethyl-4-methoxybenzenesulfonyl, Mtr: 2,3,6-trimethyl-4-methoxybenzenesulfonyl, Mts: 2,4,6-trimethylbenzenesulfonyl, Pme: pentamethylbenzenesulfonyl and the like).

Preferred examples of the substituents in the compound to be used in the present invention (the formula (I)) are given below.

A preferred example of $L^1$ is a bond.

A preferred example of $L^2$ is a bond.

A preferred example of $L^3$ is $NR^{19}$ (wherein $R^{19}$ is a hydrogen atom or a $C_{1-10}$ alkyl group). A more preferred example is NH.

A preferred example of $L^4$ is a bond or $NR^{22}$ (wherein $R^{22}$ is a hydrogen atom or a $C_{1-10}$ alkyl group). A more preferred example is a bond or NH.

Specific preferred examples of $R^1$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a $C_{1-10}$ alkyl group, a halogen atom, a $C_{1-10}$ alkyl group substituted with one or more halogen atoms, a nitro group, an amino group, an amino group substituted with one or two $C_{1-10}$ alkyl groups, an amino group substituted with a $C_{1-10}$ alkylcarbonyl group, a thiol group substituted with a $C_{1-10}$ alkyl group, a thiol group substituted with a $C_{1-10}$ alkylcarbonyl group, a hydroxyl group, a $C_{1-6}$ alkoxy group, a $C_{1-6}$ alkoxy group substituted with one or more halogen atoms, a $C_{1-10}$ alkylcarbonyloxy group, a $C_{1-10}$ alkoxycarbonyl group and a $C_{1-10}$ alkylcarbonyl group.

A particularly preferred example of $R^1$ is a phenyl group (the phenyl group is optionally substituted with one or more substitutents selected from the group consisting of a $C_{1-10}$ alkyl group (the $C_{1-10}$ alkyl group may be substituted with one or more halogen atoms), a halogen atom, a $C_{1-10}$ alkoxyl group or a $C_{1-3}$ alkoxy group (the $C_{1-3}$ alkoxy group is optionally substituted with one or more halogen atoms)).

More preferred specific examples of $R^1$ are a 3-methyl-phenyl group, a 4-methyl-phenyl group, a 3,4-dimethyl-phenyl group, a 3-t-butyl-phenyl group, a 4-t-butyl-phenyl group, a 3-trifluoromethyl-phenyl group, a 4-trifluoromethyl-phenyl group, a 4-trifluoromethoxy-phenyl group, a 3,4-ditrifluoromethyl-phenyl group, a 3-chloro-phenyl group, a 4-chloro-phenyl group, a 3-fluoro-phenyl group, a 4-fluoro-phenyl group, a 3,4-dichloro-phenyl group, a 4-methoxy-phenyl group and the like.

Still further preferred specific examples of $R^1$ are a 3,4-dimethyl-phenyl group, a 4-t-butyl-phenyl group, a 4-trifluoromethyl-phenyl group and a 4-trifluoromethoxy-phenyl group.

Specific preferable examples of the substituent $R^2$ are a hydrogen atom, a methyl group, an ethyl group, a n-propyl group, an i-propyl group, a t-butyl group and a phenyl group, particularly preferable examples are a hydrogen atom, a methyl group and an ethyl group.

Specific preferable examples of the substituent $R^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a hydroxyl group, an amino group, a carboxyl group, a phosphonic acid group, a sulfonic acid group, a carbamido group, a hydroxycarbamido group, a cyanocarbamido group, a sulfamido group, a hydroxysulfamido group, a cyanosulfamido group, a tetrazole group, $—CH_2CO_2H$, $—OCH_2CO_2H$, $—NHCH_2CO_2H$, $—CH_2CH_2CO_2H$, an alkoxycarbonyl group and the following heterocyclic groups substituted with a hydroxyl group.

Heterocyclic groups: a 1,3,4-oxadiazole group, a 1,3,4-thiadiazole group, a 1,2,4-oxadiazole group, a 1,2,4-thiadiazole group, a 1,2,5-oxadiazole group, a 1,2,5-thiadiazole group, a 1,2-oxazole group and a 1,2-thiazole group.

Still further, specific preferable examples of the substituent $R^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more substituents optionally selected from substituent set A and with one or more substituents optionally selected from substituent set B.

Substituent set A: a hydroxyl group, an amino group, a carboxyl group, a phosphonic acid group, a sulfonic acid, a carbamido group, a hydroxycarbamido group, a cyanocarbamido group, a sulfamido group, a hydroxysulfamido group, a cyanosulfamido group, a tetrazole group, —CH$_2$CO$_2$H, —OCH$_2$CO$_2$H, —NHCH$_2$CO$_2$H, —CH$_2$CH$_2$CO$_2$H and an alkoxycarbonyl group.

Substituent set B: a nitro group, a cyano group, a halogen atom, a C$_{1-10}$ alkyl group substituted with one or more fluorines, a sulfamido group substituted with one or more C$_{1-10}$ alkyl groups, a carbamido group substituted with one or more C$_{1-10}$ alkyl groups and a C$_{1-10}$ alkylcarbonylamino group.

Specific particularly preferable examples of the substituent R$^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more of the following substituents.

Substituents: a hydroxyl group, an amino group, a carboxyl group, a phosphonic acid group, a sulfonic acid group, a carbamido group, a sulfamido group, a tetrazole group, —CH$_2$CO$_2$H, —OCH$_2$CO$_2$H, —NHCH$_2$CO$_2$H and —CH$_2$CH$_2$CO$_2$H.

Still further, specific particularly preferable examples of the substituent R$^3$ are a phenyl group, thienyl groups (a 2-thienyl group and a 3-thienyl group), furyl groups (a 2-furyl group and a 3-furyl group), pyridazinyl groups (a 3-pyridazinyl group and a 4-pyridazinyl group), pyridyl groups (a 2-pyridyl group, a 3-pyridyl group and a 4-pyridyl group), quinolyl groups (a 2-quinolyl group, a 3-quinolyl group, a 4-quinolyl group, a 5-quinolyl group, a 6-quinolyl group, a 7-quinolyl group and a 8-quinolyl group) and isoquinolyl groups (a 1-isoquinolyl group, a 3-isoquinolyl group, a 4-isoquinolyl group, a 5-isoquinolyl group, a 6-isoquinolyl group, a 7-isoquinolyl group and a 8-isoquinolyl group) optionally substituted with one or more substituents optionally selected from substituent set A and with one or more substituents optionally selected from substituent set B.

Substituent set A: a hydroxyl group, an amino group, a carboxyl group, a phosphonic acid group, a sulfonic acid group, a carbamido group, a sulfamido group, a tetrazole group, —CH$_2$CO$_2$H, —OCH$_2$CO$_2$H, —NHCH$_2$CO$_2$H and —CH$_2$CH$_2$CO$_2$H.

Substituent set B: a nitro group, a cyano group, a halogen atom, a C$_{1-10}$ alkyl group substituted with one or more fluorine atoms, a sulfamido group substituted with one or more C$_{1-10}$ alkyl groups, a carbamido group substituted with one or more C$_{1-10}$ alkyl groups and a C$_{1-10}$ alkylcarbonylamino group.

Another preferred example of R$^3$ is a C$_{2-14}$ aryl group substituted with a group represented by the formula (2) (wherein R$^{37}$ is a 2-pyridyl group, a 3-pyridyl group, a 4-pyridyl group, a 2-pyridylmethyl group, a 3-pyridylmethyl group, a 4-pyridylmethyl group or an N-oxide thereof or a hydroxyl group).

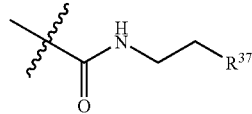

(2)

Specific preferable examples of X are OH, SH, NH$_2$, OMe, SMe, NHMe, OC(=O)CH$_3$, SC(=O)CH$_3$, NC(=O)CH$_3$ and the like, and particularly preferred examples are OH and OC(=O)CH$_3$.

Specific preferable examples of Y are an oxygen atom and a sulfur atom.

Specific preferable examples of A and B are such that the following formula (3):

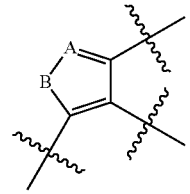

(3)

has the structure represented by the formula (4) or (5).

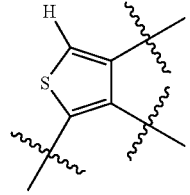

(4)

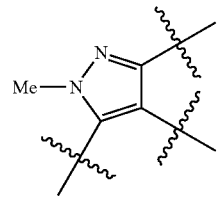

(5)

More preferable examples of A and B are such that the above formula (3) has the structure represented by the following formula (4).

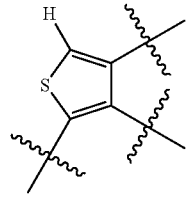

(4)

Favorable compounds to be used for the present invention are as follows.

(1) Compounds represented by the formula (6):

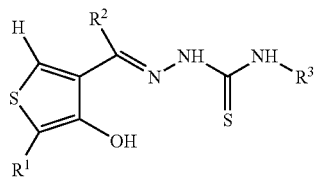

wherein $R^1$ is a phenyl group (the phenyl group is optionally substituted with a $C_{1-10}$ alkyl group (the $C_{1-10}$ alkyl group may be substituted with one or more halogen atoms), a halogen atom, a $C_{1-10}$ alkoxy group or a $C_{1-3}$ alkoxy group (the $C_{1-3}$ alkoxy group is optionally substituted with one or more halogen atoms), $R^2$ is a hydrogen atom or a $C_{1-6}$ alkyl group (the $C_{1-6}$ alkyl group may be substituted with one or more halogen atoms), and $R^3$ is a $C_{2-14}$ aryl group (the $C_{2-14}$ aryl group is optionally substituted with one or more substituents selected from the group consisting of: a hydroxyl group, an amino group, a carboxyl group, a phosphonic acid group, a sulfonic acid group, a carbamido group, a sulfamido group, a tetrazole group and a $C_{1-10}$ alkylcarbonyl group), tautomers or pharmaceutically acceptable salts of the compounds or solvates thereof.

(2) The compounds according to (1) wherein $R^2$ is a $C_{1-6}$ alkyl group, and $R^3$ is a $C_{2-14}$ aryl group (the $C_{2-14}$ aryl group is optionally substituted with one or more substituents selected from the group consisting of: a carboxyl group, a phosphonic acid group, a sulfonic acid group, a carbamido group, a sulfamido group and a tetrazole group), tautomers or pharmaceutically acceptable salts of the compounds or solvates thereof.

(3) The compounds according to (1) wherein $R^2$ is a $C_{1-3}$ alkyl group, and $R^3$ is a $C_{2-14}$ aryl group (the $C_{2-14}$ aryl group is optionally substituted with one or more substituents selected from the group consisting of: a carboxyl group, a carbamido group, a sulfamido group and a tetrazole group), tautomers or pharmaceutically acceptable salts of the compounds or solvates thereof.

(4) Compounds represented by the formula (7):

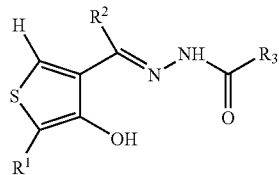

wherein $R^1$ is a phenyl group (the phenyl group is optionally substituted with a $C_{1-10}$ alkyl group (the $C_{1-10}$ alkyl group may be substituted with one or more halogen atoms), a halogen atom, a $C_{1-10}$ alkoxy group or a $C_{1-3}$ alkoxy group (the $C_{1-3}$ alkoxy group is optionally substituted with one or more halogen atoms), $R^2$ is a hydrogen atom or a $C_{1-6}$ alkyl group (the $C_{1-6}$ alkyl group may be substituted with one or more halogen atoms), and $R^3$ is a $C_{2-14}$ aryl group (the $C_{2-14}$ aryl group is optionally substituted with one or more substituents selected from the group consisting of: a hydroxyl group, an amino group, a carboxyl group, a phosphonic acid group, a sulfonic acid group, a carbamido group, a sulfamido group, a tetrazole group and a $C_{1-10}$ alkylcarbonyl group and one or more substituents selected from the group consisting of: a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers or pharmaceutically acceptable salts of the compounds or solvates thereof.

(5) The compounds according to (4) wherein $R^2$ is a $C_{1-6}$ alkyl group, and $R^3$ is a $C_{2-14}$ aryl group (the $C_{2-14}$ aryl group is optionally substituted with one or more substituents selected from the group consisting of: a carboxyl group, a phosphonic acid group, a sulfonic acid group, a carbamido group, a sulfamido group and a tetrazole group and one or more substituents selected from the group consisting of: a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers or pharmaceutically acceptable salts of the compounds or solvates thereof.

(6) The compounds according to (4) wherein $R^2$ is a $C_{1-3}$ alkyl group, and $R^3$ is a $C_{2-14}$ aryl group (the $C_{2-14}$ aryl group is optionally substituted with one or more substituents selected from the group consisting of: a carboxyl group, a carbamido group, a sulfamido group and a tetrazole group and one or more substituents selected from the group consisting of: a nitro group, a cyano group, a halogen atom, a $C_{1-10}$ alkyl group substituted with one or more fluorine atoms, a sulfamido group substituted with one or two $C_{1-10}$ alkyl groups, a carbamido group substituted with one or two $C_{1-10}$ alkyl groups and a $C_{1-10}$ alkylcarbonylamino group), tautomers or pharmaceutically acceptable salts of the compounds or solvates thereof.

(7) Compounds represented by the formula (7):

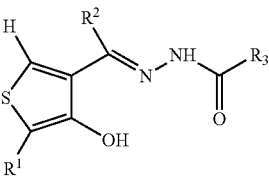

wherein $R^1$ is a phenyl group (the phenyl group is optionally substituted with a $C_{1-10}$ alkyl group (the $C_{1-10}$ alkyl group may be substituted with one or more halogen atoms), a halogen atom, a $C_{1-10}$ alkoxy group or a $C_{1-3}$ alkoxy group (the $C_{1-3}$ alkoxy group is optionally substituted with one or more halogen atoms), $R^2$ is a hydrogen atom or a $C_{1-6}$ alkyl group (the $C_{1-6}$ alkyl group may be substituted with one or more halogen atoms), and $R^3$ is a $C_{2-14}$ aryl group (the $C_{2-14}$ aryl group is optionally substituted with a hydroxyl group, an amino group, a carboxyl group, a phosphonic acid group, a sulfonic acid group, a carbamido group, a sulfamido group, a tetrazole group or a $C_{1-10}$ alkoxycarbonyl group), tautomers or pharmaceutically acceptable salts of the compounds or solvates thereof.

(8) The compounds according to (7), wherein $R^2$ is a $C_{1-6}$ alkyl group, and $R^3$ is a $C_{2-14}$ aryl group (the $C_{2-14}$ aryl group is optionally substituted with a carboxyl group, a phosphonic acid group, a sulfonic acid group, a carbamido group, a sulfamido group or a tetrazole group), tautomers or pharmaceutically acceptable salts of the compounds or solvates thereof.

(9) The compounds according to (7), wherein $R^2$ is a $C_{1-3}$ alkyl group, and $R^3$ is a $C_{2-14}$ aryl group (the $C_{2-14}$ aryl group is optionally substituted with a carboxyl group, a sulfamido group or a tetrazole group), tautomers or pharmaceutically acceptable salts of the compounds or solvates thereof.

(10) Compounds represented by the formula (7):

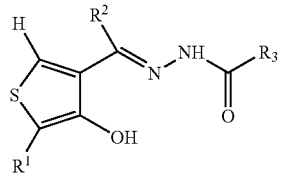

(7)

wherein $R^1$ is a phenyl group (the phenyl group is optionally substituted with a $C_{1-10}$ alkyl group (the $C_{1-10}$ alkyl group may be substituted with one or more halogen atoms), a halogen atom, a $C_{1-10}$ alkoxy group or a $C_{1-3}$ alkoxy group (the $C_{1-3}$ alkoxy group is optionally substituted with one or more halogen atoms), $R^2$ is a hydrogen atom or a $C_{1-6}$ alkyl group (the $C_{1-6}$ alkyl group may be substituted with one or more halogen atoms), and $R^3$ is a $C_{2-14}$ aryl group substituted with a group represented by the formula (2):

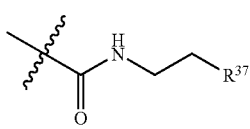

(2)

(wherein $R^{37}$ is a 2-pyridyl group, a 3-pyridyl group, a 4-pyridyl group, a 2-pyridylmethyl group, a 3-pyridylmethyl group, a 4-pyridyl methyl group or an N-oxide thereof or a hydroxyl group), tautomers or pharmaceutically acceptable salts of the compounds or solvates thereof.

(11) The compounds according to (10), wherein $R^2$ is a $C_{1-6}$ alkyl group, tautomers or pharmaceutically acceptable salts of the compounds or solvates thereof.

(12) The compounds according to (11), wherein $R^2$ is a $C_{1-3}$ alkyl group, tautomers or pharmaceutically acceptable salts of the compounds or solvates thereof.

(13) The compounds according to any of (1) to (12), wherein the $C_{2-14}$ aryl group as $R^3$ is a phenyl group, tautomers or pharmaceutically acceptable salts of the compounds or solvates thereof.

(14) The compounds according to any of (1) to (12), wherein the $C_{2-14}$ aryl group as $R^3$ is a 2-thienyl group, tautomers or pharmaceutically acceptable salts of the compounds or solvates thereof.

(15) Compounds of the formula (8) wherein A, B, $R^1$, $R^3$, $L^4$ and Y are any of the following combinations in Table 1, tautomers or pharmaceutically acceptable salts of the compounds or solvates thereof. The symbols in Table 1 denote the following substituents.

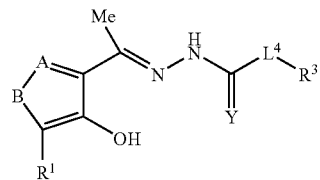

(8)

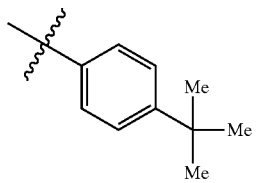

Ra1

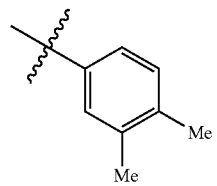

Ra2

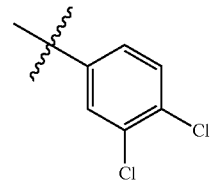

Ra3

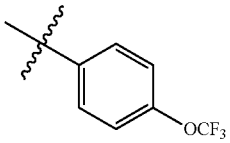

Ra4

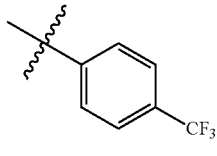

Ra5

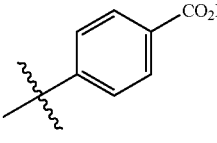

Q1

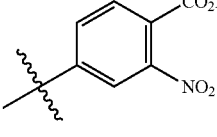

Q2

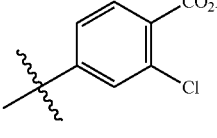

Q3

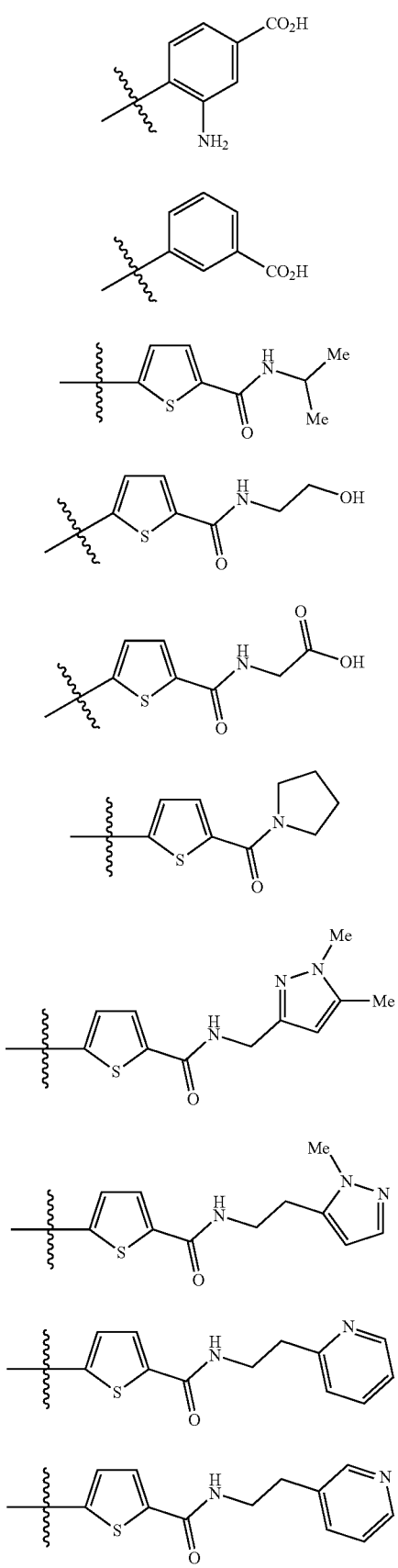
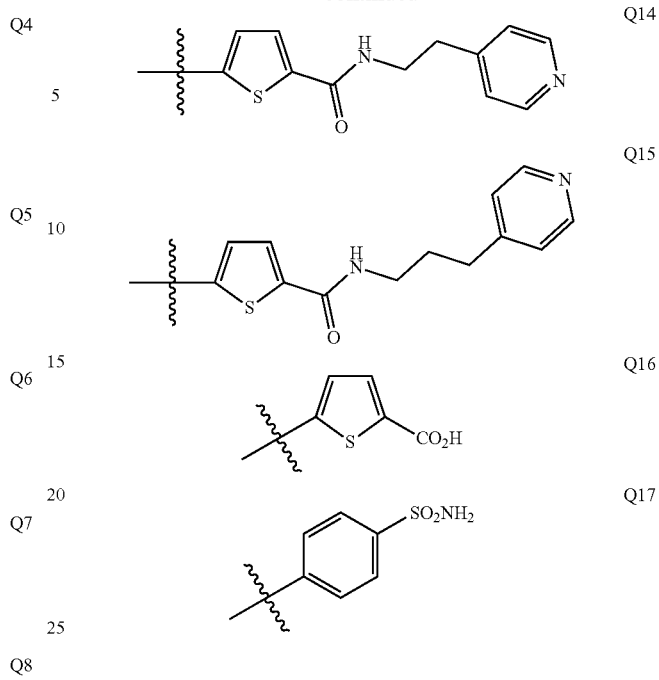

TABLE 1

| No | A | B | R¹ | R³ | L4 | Y |
|---|---|---|---|---|---|---|
| 1 | CH | S | Ra1 | Q1 | bond | O |
| 2 | CH | S | Ra1 | Q2 | bond | O |
| 3 | CH | S | Ra1 | Q3 | bond | O |
| 4 | CH | S | Ra1 | Q4 | bond | O |
| 5 | CH | S | Ra1 | Q5 | bond | O |
| 6 | CH | S | Ra1 | Q6 | bond | O |
| 7 | CH | S | Ra1 | Q7 | bond | O |
| 8 | CH | S | Ra1 | Q8 | bond | O |
| 9 | CH | S | Ra1 | Q9 | bond | O |
| 10 | CH | S | Ra1 | Q10 | bond | O |
| 11 | CH | S | Ra1 | Q11 | bond | O |
| 12 | CH | S | Ra1 | Q12 | bond | O |
| 13 | CH | S | Ra1 | Q13 | bond | O |
| 14 | CH | S | Ra1 | Q14 | bond | O |
| 15 | CH | S | Ra1 | Q15 | bond | O |
| 16 | CH | S | Ra1 | Q16 | bond | O |
| 17 | CH | S | Ra1 | Q17 | bond | O |
| 18 | CH | S | Ra2 | Q1 | bond | O |
| 19 | CH | S | Ra2 | Q2 | bond | O |
| 20 | CH | S | Ra2 | Q3 | bond | O |
| 21 | CH | S | Ra2 | Q4 | bond | O |
| 22 | CH | S | Ra2 | Q5 | bond | O |
| 23 | CH | S | Ra2 | Q6 | bond | O |
| 24 | CH | S | Ra2 | Q7 | bond | O |
| 25 | CH | S | Ra2 | Q8 | bond | O |
| 26 | CH | S | Ra2 | Q9 | bond | O |
| 27 | CH | S | Ra2 | Q10 | bond | O |
| 28 | CH | S | Ra2 | Q11 | bond | O |
| 29 | CH | S | Ra2 | Q12 | bond | O |
| 30 | CH | S | Ra2 | Q13 | bond | O |
| 31 | CH | S | Ra2 | Q14 | bond | O |
| 32 | CH | S | Ra2 | Q15 | bond | O |
| 33 | CH | S | Ra2 | Q16 | bond | O |
| 34 | CH | S | Ra2 | Q17 | bond | O |
| 35 | CH | S | Ra3 | Q1 | bond | O |
| 36 | CH | S | Ra3 | Q2 | bond | O |
| 37 | CH | S | Ra3 | Q3 | bond | O |
| 38 | CH | S | Ra3 | Q4 | bond | O |
| 39 | CH | S | Ra3 | Q5 | bond | O |
| 40 | CH | S | Ra3 | Q6 | bond | O |
| 41 | CH | S | Ra3 | Q7 | bond | O |
| 42 | CH | S | Ra3 | Q8 | bond | O |
| 43 | CH | S | Ra3 | Q9 | bond | O |
| 44 | CH | S | Ra3 | Q10 | bond | O |

TABLE 1-continued

| No | A | B | R¹ | R³ | L4 | Y |
|---|---|---|---|---|---|---|
| 45 | CH | S | Ra3 | Q11 | bond | O |
| 46 | CH | S | Ra3 | Q12 | bond | O |
| 47 | CH | S | Ra3 | Q13 | bond | O |
| 48 | CH | S | Ra3 | Q14 | bond | O |
| 49 | CH | S | Ra3 | Q15 | bond | O |
| 50 | CH | S | Ra3 | Q16 | bond | O |
| 51 | CH | S | Ra3 | Q17 | bond | O |
| 52 | CH | S | Ra4 | Q1 | bond | O |
| 53 | CH | S | Ra4 | Q2 | bond | O |
| 54 | CH | S | Ra4 | Q3 | bond | O |
| 55 | CH | S | Ra4 | Q4 | bond | O |
| 56 | CH | S | Ra4 | Q5 | bond | O |
| 57 | CH | S | Ra4 | Q6 | bond | O |
| 58 | CH | S | Ra4 | Q7 | bond | O |
| 59 | CH | S | Ra4 | Q8 | bond | O |
| 60 | CH | S | Ra4 | Q9 | bond | O |
| 61 | CH | S | Ra4 | Q10 | bond | O |
| 62 | CH | S | Ra4 | Q11 | bond | O |
| 63 | CH | S | Ra4 | Q12 | bond | O |
| 64 | CH | S | Ra4 | Q13 | bond | O |
| 65 | CH | S | Ra4 | Q14 | bond | O |
| 66 | CH | S | Ra4 | Q15 | bond | O |
| 67 | CH | S | Ra4 | Q16 | bond | O |
| 68 | CH | S | Ra4 | Q17 | bond | O |
| 69 | CH | S | Ra5 | Q1 | bond | O |
| 70 | CH | S | Ra5 | Q2 | bond | O |
| 71 | CH | S | Ra5 | Q3 | bond | O |
| 72 | CH | S | Ra5 | Q4 | bond | O |
| 73 | CH | S | Ra5 | Q5 | bond | O |
| 74 | CH | S | Ra5 | Q6 | bond | O |
| 75 | CH | S | Ra5 | Q7 | bond | O |
| 76 | CH | S | Ra5 | Q8 | bond | O |
| 77 | CH | S | Ra5 | Q9 | bond | O |
| 78 | CH | S | Ra5 | Q10 | bond | O |
| 79 | CH | S | Ra5 | Q11 | bond | O |
| 80 | CH | S | Ra5 | Q12 | bond | O |
| 81 | CH | S | Ra5 | Q13 | bond | O |
| 82 | CH | S | Ra5 | Q14 | bond | O |
| 83 | CH | S | Ra5 | Q15 | bond | O |
| 84 | CH | S | Ra5 | Q16 | bond | O |
| 85 | CH | S | Ra5 | Q17 | bond | O |
| 86 | CH | S | Ra1 | Q1 | NH | S |
| 87 | CH | S | Ra1 | Q2 | NH | S |
| 88 | CH | S | Ra1 | Q3 | NH | S |
| 89 | CH | S | Ra1 | Q4 | NH | S |
| 90 | CH | S | Ra1 | Q5 | NH | S |
| 91 | CH | S | Ra1 | Q6 | NH | S |
| 92 | CH | S | Ra1 | Q7 | NH | S |
| 93 | CH | S | Ra1 | Q8 | NH | S |
| 94 | CH | S | Ra1 | Q9 | NH | S |
| 95 | CH | S | Ra1 | Q10 | NH | S |
| 96 | CH | S | Ra1 | Q11 | NH | S |
| 97 | CH | S | Ra1 | Q12 | NH | S |
| 98 | CH | S | Ra1 | Q13 | NH | S |
| 99 | CH | S | Ra1 | Q14 | NH | S |
| 100 | CH | S | Ra1 | Q15 | NH | S |
| 101 | CH | S | Ra1 | Q16 | NH | S |
| 102 | CH | S | Ra1 | Q17 | NH | S |
| 103 | CH | S | Ra2 | Q1 | NH | S |
| 104 | CH | S | Ra2 | Q2 | NH | S |
| 105 | CH | S | Ra2 | Q3 | NH | S |
| 106 | CH | S | Ra2 | Q4 | NH | S |
| 107 | CH | S | Ra2 | Q5 | NH | S |
| 108 | CH | S | Ra2 | Q6 | NH | S |
| 109 | CH | S | Ra2 | Q7 | NH | S |
| 110 | CH | S | Ra2 | Q8 | NH | S |
| 111 | CH | S | Ra2 | Q9 | NH | S |
| 112 | CH | S | Ra2 | Q10 | NH | S |
| 113 | CH | S | Ra2 | Q11 | NH | S |
| 114 | CH | S | Ra2 | Q12 | NH | S |
| 115 | CH | S | Ra2 | Q13 | NH | S |
| 116 | CH | S | Ra2 | Q14 | NH | S |
| 117 | CH | S | Ra2 | Q15 | NH | S |
| 118 | CH | S | Ra2 | Q16 | NH | S |
| 119 | CH | S | Ra2 | Q17 | NH | S |
| 120 | CH | S | Ra3 | Q1 | NH | S |
| 121 | CH | S | Ra3 | Q2 | NH | S |
| 122 | CH | S | Ra3 | Q3 | NH | S |
| 123 | CH | S | Ra3 | Q4 | NH | S |
| 124 | CH | S | Ra3 | Q5 | NH | S |
| 125 | CH | S | Ra3 | Q6 | NH | S |
| 126 | CH | S | Ra3 | Q7 | NH | S |
| 127 | CH | S | Ra3 | Q8 | NH | S |
| 128 | CH | S | Ra3 | Q9 | NH | S |
| 129 | CH | S | Ra3 | Q10 | NH | S |
| 130 | CH | S | Ra3 | Q11 | NH | S |
| 131 | CH | S | Ra3 | Q12 | NH | S |
| 132 | CH | S | Ra3 | Q13 | NH | S |
| 133 | CH | S | Ra3 | Q14 | NH | S |
| 134 | CH | S | Ra3 | Q15 | NH | S |
| 135 | CH | S | Ra3 | Q16 | NH | S |
| 136 | CH | S | Ra3 | Q17 | NH | S |
| 137 | CH | S | Ra4 | Q1 | NH | S |
| 138 | CH | S | Ra4 | Q2 | NH | S |
| 139 | CH | S | Ra4 | Q3 | NH | S |
| 140 | CH | S | Ra4 | Q4 | NH | S |
| 141 | CH | S | Ra4 | Q5 | NH | S |
| 142 | CH | S | Ra4 | Q6 | NH | S |
| 143 | CH | S | Ra4 | Q7 | NH | S |
| 144 | CH | S | Ra4 | Q8 | NH | S |
| 145 | CH | S | Ra4 | Q9 | NH | S |
| 146 | CH | S | Ra4 | Q10 | NH | S |
| 147 | CH | S | Ra4 | Q11 | NH | S |
| 148 | CH | S | Ra4 | Q12 | NH | S |
| 149 | CH | S | Ra4 | Q13 | NH | S |
| 150 | CH | S | Ra4 | Q14 | NH | S |
| 151 | CH | S | Ra4 | Q15 | NH | S |
| 152 | CH | S | Ra4 | Q16 | NH | S |
| 153 | CH | S | Ra4 | Q17 | NH | S |
| 154 | CH | S | Ra5 | Q1 | NH | S |
| 155 | CH | S | Ra5 | Q2 | NH | S |
| 156 | CH | S | Ra5 | Q3 | NH | S |
| 157 | CH | S | Ra5 | Q4 | NH | S |
| 158 | CH | S | Ra5 | Q5 | NH | S |
| 159 | CH | S | Ra5 | Q6 | NH | S |
| 160 | CH | S | Ra5 | Q7 | NH | S |
| 161 | CH | S | Ra5 | Q8 | NH | S |
| 162 | CH | S | Ra5 | Q9 | NH | S |
| 163 | CH | S | Ra5 | Q10 | NH | S |
| 164 | CH | S | Ra5 | Q11 | NH | S |
| 165 | CH | S | Ra5 | Q12 | NH | S |
| 166 | CH | S | Ra5 | Q13 | NH | S |
| 167 | CH | S | Ra5 | Q14 | NH | S |
| 168 | CH | S | Ra5 | Q15 | NH | S |
| 169 | CH | S | Ra5 | Q16 | NH | S |
| 170 | CH | S | Ra5 | Q17 | NH | S |
| 171 | N | N—Me | Ra1 | Q1 | bond | O |
| 172 | N | N—Me | Ra1 | Q2 | bond | O |
| 173 | N | N—Me | Ra1 | Q3 | bond | O |
| 174 | N | N—Me | Ra1 | Q4 | bond | O |
| 175 | N | N—Me | Ra1 | Q5 | bond | O |
| 176 | N | N—Me | Ra1 | Q6 | bond | O |
| 177 | N | N—Me | Ra1 | Q7 | bond | O |
| 178 | N | N—Me | Ra1 | Q8 | bond | O |
| 179 | N | N—Me | Ra1 | Q9 | bond | O |
| 180 | N | N—Me | Ra1 | Q10 | bond | O |
| 181 | N | N—Me | Ra1 | Q11 | bond | O |
| 182 | N | N—Me | Ra1 | Q12 | bond | O |
| 183 | N | N—Me | Ra1 | Q13 | bond | O |
| 184 | N | N—Me | Ra1 | Q14 | bond | O |
| 185 | N | N—Me | Ra1 | Q15 | bond | O |
| 186 | N | N—Me | Ra1 | Q16 | bond | O |
| 187 | N | N—Me | Ra1 | Q17 | bond | O |
| 188 | N | N—Me | Ra2 | Q1 | bond | O |
| 189 | N | N—Me | Ra2 | Q2 | bond | O |
| 190 | N | N—Me | Ra2 | Q3 | bond | O |
| 191 | N | N—Me | Ra2 | Q4 | bond | O |
| 192 | N | N—Me | Ra2 | Q5 | bond | O |
| 193 | N | N—Me | Ra2 | Q6 | bond | O |
| 194 | N | N—Me | Ra2 | Q7 | bond | O |
| 195 | N | N—Me | Ra2 | Q8 | bond | O |
| 196 | N | N—Me | Ra2 | Q9 | bond | O |
| 197 | N | N—Me | Ra2 | Q10 | bond | O |
| 198 | N | N—Me | Ra2 | Q11 | bond | O |
| 199 | N | N—Me | Ra2 | Q12 | bond | O |
| 200 | N | N—Me | Ra2 | Q13 | bond | O |

TABLE 1-continued

| No | A | B | R¹ | R³ | L4 | Y |
|---|---|---|---|---|---|---|
| 201 | N | N—Me | Ra2 | Q14 | bond | O |
| 202 | N | N—Me | Ra2 | Q15 | bond | O |
| 203 | N | N—Me | Ra2 | Q16 | bond | O |
| 204 | N | N—Me | Ra2 | Q17 | bond | O |
| 205 | N | N—Me | Ra3 | Q1 | bond | O |
| 206 | N | N—Me | Ra3 | Q2 | bond | O |
| 207 | N | N—Me | Ra3 | Q3 | bond | O |
| 208 | N | N—Me | Ra3 | Q4 | bond | O |
| 209 | N | N—Me | Ra3 | Q5 | bond | O |
| 210 | N | N—Me | Ra3 | Q6 | bond | O |
| 211 | N | N—Me | Ra3 | Q7 | bond | O |
| 212 | N | N—Me | Ra3 | Q8 | bond | O |
| 213 | N | N—Me | Ra3 | Q9 | bond | O |
| 214 | N | N—Me | Ra3 | Q10 | bond | O |
| 215 | N | N—Me | Ra3 | Q11 | bond | O |
| 216 | N | N—Me | Ra3 | Q12 | bond | O |
| 217 | N | N—Me | Ra3 | Q13 | bond | O |
| 218 | N | N—Me | Ra3 | Q14 | bond | O |
| 219 | N | N—Me | Ra3 | Q15 | bond | O |
| 220 | N | N—Me | Ra3 | Q16 | bond | O |
| 221 | N | N—Me | Ra3 | Q17 | bond | O |
| 222 | N | N—Me | Ra4 | Q1 | bond | O |
| 223 | N | N—Me | Ra4 | Q2 | bond | O |
| 224 | N | N—Me | Ra4 | Q3 | bond | O |
| 225 | N | N—Me | Ra4 | Q4 | bond | O |
| 226 | N | N—Me | Ra4 | Q5 | bond | O |
| 227 | N | N—Me | Ra4 | Q6 | bond | O |
| 228 | N | N—Me | Ra4 | Q7 | bond | O |
| 229 | N | N—Me | Ra4 | Q8 | bond | O |
| 230 | N | N—Me | Ra4 | Q9 | bond | O |
| 231 | N | N—Me | Ra4 | Q10 | bond | O |
| 232 | N | N—Me | Ra4 | Q11 | bond | O |
| 233 | N | N—Me | Ra4 | Q12 | bond | O |
| 234 | N | N—Me | Ra4 | Q13 | bond | O |
| 235 | N | N—Me | Ra4 | Q14 | bond | O |
| 236 | N | N—Me | Ra4 | Q15 | bond | O |
| 237 | N | N—Me | Ra4 | Q16 | bond | O |
| 238 | N | N—Me | Ra4 | Q17 | bond | O |
| 239 | N | N—Me | Ra5 | Q1 | bond | O |
| 240 | N | N—Me | Ra5 | Q2 | bond | O |
| 241 | N | N—Me | Ra5 | Q3 | bond | O |
| 242 | N | N—Me | Ra5 | Q4 | bond | O |
| 243 | N | N—Me | Ra5 | Q5 | bond | O |
| 244 | N | N—Me | Ra5 | Q6 | bond | O |
| 245 | N | N—Me | Ra5 | Q7 | bond | O |
| 246 | N | N—Me | Ra5 | Q8 | bond | O |
| 247 | N | N—Me | Ra5 | Q9 | bond | O |
| 248 | N | N—Me | Ra5 | Q10 | bond | O |
| 249 | N | N—Me | Ra5 | Q11 | bond | O |
| 250 | N | N—Me | Ra5 | Q12 | bond | O |
| 251 | N | N—Me | Ra5 | Q13 | bond | O |
| 252 | N | N—Me | Ra5 | Q14 | bond | O |
| 253 | N | N—Me | Ra5 | Q15 | bond | O |
| 254 | N | N—Me | Ra5 | Q16 | bond | O |
| 255 | N | N—Me | Ra5 | Q17 | bond | O |
| 256 | N | N—Me | Ra1 | Q1 | NH | S |
| 257 | N | N—Me | Ra1 | Q2 | NH | S |
| 258 | N | N—Me | Ra1 | Q3 | NH | S |
| 259 | N | N—Me | Ra1 | Q4 | NH | S |
| 260 | N | N—Me | Ra1 | Q5 | NH | S |
| 261 | N | N—Me | Ra1 | Q6 | NH | S |
| 262 | N | N—Me | Ra1 | Q7 | NH | S |
| 263 | N | N—Me | Ra1 | Q8 | NH | S |
| 264 | N | N—Me | Ra1 | Q9 | NH | S |
| 265 | N | N—Me | Ra1 | Q10 | NH | S |
| 266 | N | N—Me | Ra1 | Q11 | NH | S |
| 267 | N | N—Me | Ra1 | Q12 | NH | S |
| 268 | N | N—Me | Ra1 | Q13 | NH | S |
| 269 | N | N—Me | Ra1 | Q14 | NH | S |
| 270 | N | N—Me | Ra1 | Q15 | NH | S |
| 271 | N | N—Me | Ra1 | Q16 | NH | S |
| 272 | N | N—Me | Ra1 | Q17 | NH | S |
| 273 | N | N—Me | Ra2 | Q1 | NH | S |
| 274 | N | N—Me | Ra2 | Q2 | NH | S |
| 275 | N | N—Me | Ra2 | Q3 | NH | S |
| 276 | N | N—Me | Ra2 | Q4 | NH | S |
| 277 | N | N—Me | Ra2 | Q5 | NH | S |
| 278 | N | N—Me | Ra2 | Q6 | NH | S |
| 279 | N | N—Me | Ra2 | Q7 | NH | S |
| 280 | N | N—Me | Ra2 | Q8 | NH | S |
| 281 | N | N—Me | Ra2 | Q9 | NH | S |
| 282 | N | N—Me | Ra2 | Q10 | NH | S |
| 283 | N | N—Me | Ra2 | Q11 | NH | S |
| 284 | N | N—Me | Ra2 | Q12 | NH | S |
| 285 | N | N—Me | Ra2 | Q13 | NH | S |
| 286 | N | N—Me | Ra2 | Q14 | NH | S |
| 287 | N | N—Me | Ra2 | Q15 | NH | S |
| 288 | N | N—Me | Ra2 | Q16 | NH | S |
| 289 | N | N—Me | Ra2 | Q17 | NH | S |
| 290 | N | N—Me | Ra3 | Q1 | NH | S |
| 291 | N | N—Me | Ra3 | Q2 | NH | S |
| 292 | N | N—Me | Ra3 | Q3 | NH | S |
| 293 | N | N—Me | Ra3 | Q4 | NH | S |
| 294 | N | N—Me | Ra3 | Q5 | NH | S |
| 295 | N | N—Me | Ra3 | Q6 | NH | S |
| 296 | N | N—Me | Ra3 | Q7 | NH | S |
| 297 | N | N—Me | Ra3 | Q8 | NH | S |
| 298 | N | N—Me | Ra3 | Q9 | NH | S |
| 299 | N | N—Me | Ra3 | Q10 | NH | S |
| 300 | N | N—Me | Ra3 | Q11 | NH | S |
| 301 | N | N—Me | Ra3 | Q12 | NH | S |
| 302 | N | N—Me | Ra3 | Q13 | NH | S |
| 303 | N | N—Me | Ra3 | Q14 | NH | S |
| 304 | N | N—Me | Ra3 | Q15 | NH | S |
| 305 | N | N—Me | Ra3 | Q16 | NH | S |
| 306 | N | N—Me | Ra3 | Q17 | NH | S |
| 307 | N | N—Me | Ra4 | Q1 | NH | S |
| 308 | N | N—Me | Ra4 | Q2 | NH | S |
| 309 | N | N—Me | Ra4 | Q3 | NH | S |
| 310 | N | N—Me | Ra4 | Q4 | NH | S |
| 311 | N | N—Me | Ra4 | Q5 | NH | S |
| 312 | N | N—Me | Ra4 | Q6 | NH | S |
| 313 | N | N—Me | Ra4 | Q7 | NH | S |
| 314 | N | N—Me | Ra4 | Q8 | NH | S |
| 315 | N | N—Me | Ra4 | Q9 | NH | S |
| 316 | N | N—Me | Ra4 | Q10 | NH | S |
| 317 | N | N—Me | Ra4 | Q11 | NH | S |
| 318 | N | N—Me | Ra4 | Q12 | NH | S |
| 319 | N | N—Me | Ra4 | Q13 | NH | S |
| 320 | N | N—Me | Ra4 | Q14 | NH | S |
| 321 | N | N—Me | Ra4 | Q15 | NH | S |
| 322 | N | N—Me | Ra4 | Q16 | NH | S |
| 323 | N | N—Me | Ra4 | Q17 | NH | S |
| 324 | N | N—Me | Ra5 | Q1 | NH | S |
| 325 | N | N—Me | Ra5 | Q2 | NH | S |
| 326 | N | N—Me | Ra5 | Q3 | NH | S |
| 327 | N | N—Me | Ra5 | Q4 | NH | S |
| 328 | N | N—Me | Ra5 | Q5 | NH | S |
| 329 | N | N—Me | Ra5 | Q6 | NH | S |
| 330 | N | N—Me | Ra5 | Q7 | NH | S |
| 331 | N | N—Me | Ra5 | Q8 | NH | S |
| 332 | N | N—Me | Ra5 | Q9 | NH | S |
| 333 | N | N—Me | Ra5 | Q10 | NH | S |
| 334 | N | N—Me | Ra5 | Q11 | NH | S |
| 335 | N | N—Me | Ra5 | Q12 | NH | S |
| 336 | N | N—Me | Ra5 | Q13 | NH | S |
| 337 | N | N—Me | Ra5 | Q14 | NH | S |
| 338 | N | N—Me | Ra5 | Q15 | NH | S |
| 339 | N | N—Me | Ra5 | Q16 | NH | S |
| 340 | N | N—Me | Ra5 | Q17 | NH | S |

The compound of the present invention can be synthesized by reference to Patent Document WO2004/108683.

The compound of the present invention represented by the formula (I) or a pharmaceutically acceptable salt thereof may be in the form of arbitrary crystals or an arbitrary hydrate, depending on the production conditions. The present invention covers these crystals, hydrates and mixtures. They may be in the form of a solvate with an organic solvent such as acetone, ethanol and tetrahydrofuran, and the present invention covers any of these forms. The compound of the present invention represented by the formula (I) may be converted to a pharmaceutically acceptable salt or may be liberated from the resulting salt, if necessary. The pharmaceutically acceptable salt of the present invention may be, for example, a salt with an alkali metal (such as lithium, sodium and potassium), an alkaline earth metal (such as magnesium and calcium), ammonium, an organic base or an amino acid. It may be a salt with an inorganic acid (such as hydrochloric acid, hydrobromic acid, phosphoric acid and sulfuric acid) or an organic acid (such as acetic acid, citric acid, maleic acid, fumaric acid, benzenesulfonic acid and p-toluenesulfonic acid).

EXAMPLES

Now, the present invention will be described in further detail with reference to Examples. However, it should be understood that the present invention is by no means restricted by these specific Examples.

Example

Expansion of CD34+ Cells from Human Cord Blood-Derived CD34+ Cells

Commercially available human cord blood-derived CD34+ cells (Cambrex Bio Science Walkersville) were plated on a 12-well plate (Corning) (from 5000 to 10000 cells/1 ml/well). As the culture medium, StemSpan SFEM (Stemcell Technologies) containing 100 ng/mL SCF (R&D Systems) was used, and Compounds Nos. 1 to 37 dissolved in dimethyl sulfoxide were added in an amount of 0.1% (v/v) to a final concentration of 0.3 or 1 μg/mL.

After the cells were incubated in liquid culture at 37° C. for 7 days in a $CO_2$ incubator (in an atmosphere containing 5 vol % $CO_2$), the total number of cells was counted by trypan blue assay (Invitrogen) or Flow-Count™ fluorosphere assay (Beckman Coulter). The number of CD34+ cells was calculated as follows. After the incubation, the cells in the liquid culture was stained with a CD34 antibody (PE, Becton, Dickinson and Company). The stained cells were analyzed with a flow cytometer (Beckman Coulter) to determined the proportion of CD34+ cells, which was multiplied by the total number of cells to calculate the number of CD34+ cells.

The results demonstrate that the compounds of the present invention showed excellent expansion activity on CD34+ cells and have expansion activity on hematopoietic stem cells and hematopoietic progenitor cells.

The expansion efficiencies in the presence of 0.3 μg/mL or 1 μg/mL of compounds based on the number of CD34+ cells in the absence of them are shown in Table 2 on a scale of A for expansion efficiencies of 3 or greater, and B for expansion efficiencies of at least 2 and less than 3.

TABLE 2

| Compound No. | Concentration of compound μg/mL | Expansion efficiency |
|---|---|---|
| 1 | 1 | A |
| 2 | 1 | B |
| 3 | 1 | A |
| 4 | 1 | A |
| 5 | 1 | B |
| 6 | 1 | B |
| 7 | 1 | A |
| 8 | 1 | A |
| 9 | 1 | A |
| 10 | 1 | A |
| 11 | 1 | A |
| 12 | 1 | A |

TABLE 2-continued

| Compound No. | Concentration of compound μg/mL | Expansion efficiency |
|---|---|---|
| 13 | 1 | A |
| 14 | 1 | A |
| 15 | 1 | A |
| 16 | 1 | B |
| 17 | 1 | A |
| 18 | 1 | A |
| 19 | 1 | A |
| 20 | 1 | A |
| 21 | 1 | A |
| 22 | 1 | A |
| 23 | 1 | B |
| 24 | 1 | A |
| 25 | 1 | A |
| 26 | 1 | A |
| 27 | 0.3 | B |
| 28 | 1 | A |
| 29 | 0.3 | A |
| 30 | 0.3 | A |
| 31 | 0.3 | A |
| 32 | 0.3 | A |
| 33 | 0.3 | A |
| 34 | 1 | A |
| 35 | 1 | A |
| 36 | 1 | A |
| 37 | 1 | A |

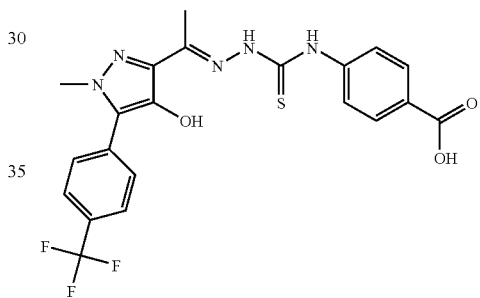

No. 1

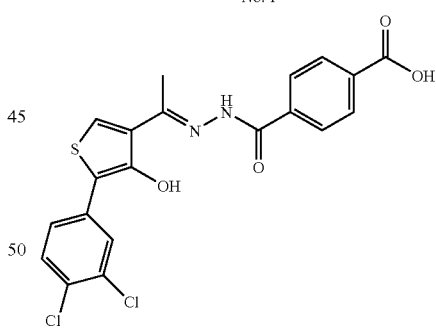

No. 2

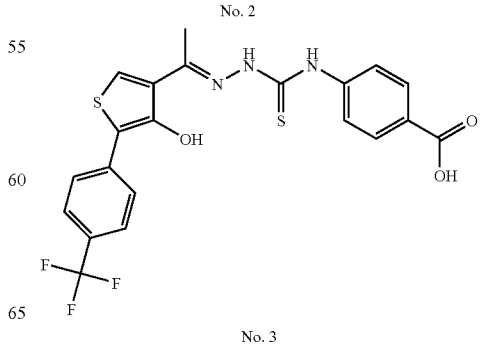

No. 3

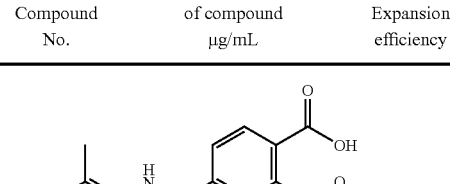

TABLE 2-continued

| Compound No. | Concentration of compound µg/mL | Expansion efficiency |
|---|---|---|

No. 12

No. 13

No. 14

No. 15

No. 16

No. 17

No. 18

No. 19

TABLE 2-continued
| Compound No. | Concentration of compound µg/mL | Expansion efficiency |
|---|---|---|
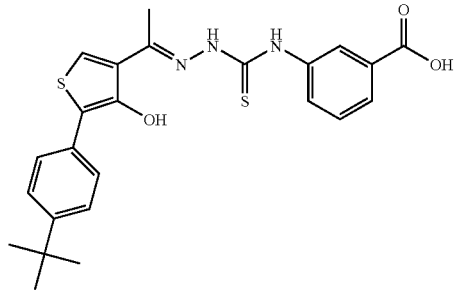
No. 20
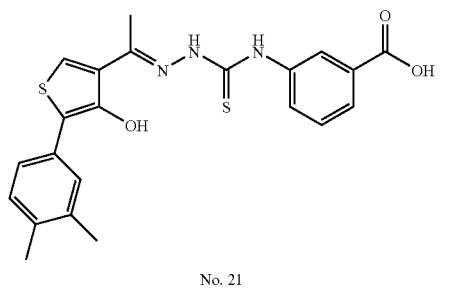 [SMILES: C/C(=N\NC(=S)Nc1cccc(C(=O)O)c1)c1csc(-c2ccc(C)c(C)c2)c1O]
No. 21
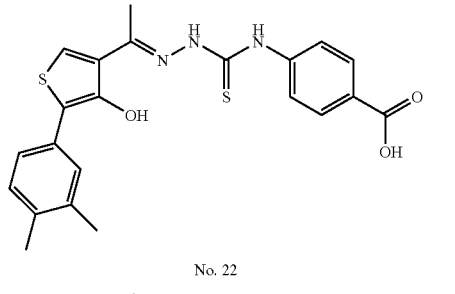 [SMILES: C/C(=N\NC(=S)Nc1ccc(C(=O)O)cc1)c1csc(-c2ccc(C)c(C)c2)c1O]
No. 22
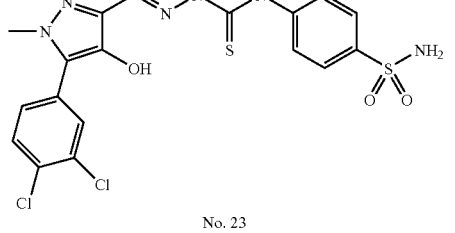
No. 23
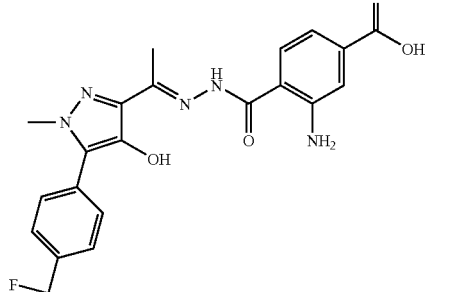
No. 24
TABLE 2-continued
| Compound No. | Concentration of compound µg/mL | Expansion efficiency |
|---|---|---|
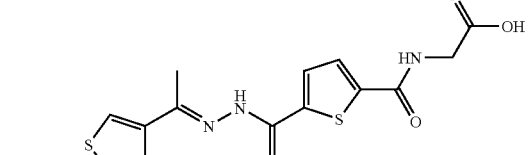
No. 25
No. 26
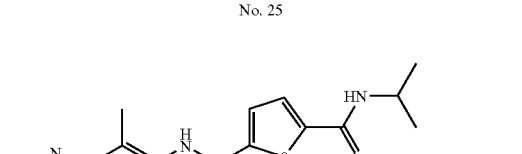
No. 27
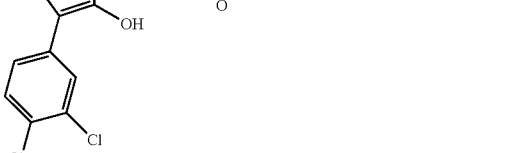
No. 28

TABLE 2-continued

| Compound No. | Concentration of compound μg/mL | Expansion efficiency |
|---|---|---|

No. 29

No. 30

No. 31

No. 32

No. 33

No. 34

No. 35

TABLE 2-continued

| Compound No. | Concentration of compound μg/mL | Expansion efficiency |
| --- | --- | --- |

No. 36

No. 37

INDUSTRIAL APPLICABILITY

The method of the present invention can expand human CD34⁺ cells by using a low molecular weight compound as an active ingredient. Cells expanded by the method of the present invention are useful as a hematopoietic cell and hematopoietic progenitor cell transplant for diseases accompanying hematopoietic dysfunction, ischemia or immune dysfunction and hence its application to cell therapy is expected.

The entire disclosure of Japanese Patent Application No. 2007-315168 filed on Dec. 5, 2007 including specification, claims and summary is incorporated herein by reference in its entirety.

The invention claimed is:

1. A method for expanding CD34⁺ cells, the method comprising:
contacting CD34⁺ cells, in an ex vivo culture, with a stem cell factor (SCF) and a compound of formula (1), a tautomer, or pharmaceutically acceptable salt of the compound or a solvate thereof:

(1)

wherein:
A is a nitrogen atom or CH,
B is a sulfur atom or $NR^9$
wherein $R^9$ is a methyl group,
$R^1$ is a phenyl group
wherein the phenyl group is substituted with one or two substituents selected from the group consisting of: a halogen atom, a $C_{1-10}$ alkyl group, a trifluoromethyl group, and a trifluoromethoxy group;
$L^1$ is a bond,
X is OH,
$R^2$ is a methyl group,
$L^2$ is a bond,
$L^3$ is NH,
$L^4$ is a bond or NH,
Y is an oxygen atom or a sulfur atom, and
$R^3$ is a phenyl group substituted with $SO_2NH_2$,
a phenyl group substituted with a carboxy group,
a phenyl group substituted with a carboxy group and a substituent selected from the group consisting of an amino group, a halogen atom, and a nitro group,
a thienyl group substituted with a carboxy group, or
a thienyl group substituted by a group represented by formula (2):

(2)

wherein $R^{37}$ is a 2-pyridyl group, a 3-pyridyl group, a 4-pyridyl group, a 4-pyridylmethyl group, or a hydroxyl group.

2. The method of claim 1, wherein A is CH and B is a sulfur atom.

3. The method of claim 1, wherein $L^4$ is NH.

4. The method of claim 1, wherein $L^4$ is a bond.

5. The method of claim 4, wherein Y is an oxygen atom.

6. The method of claim 3, wherein Y is a sulfur atom.

7. The method of claim 6, wherein $R^3$ is a phenyl group substituted with a carboxyl group.

8. The method of claim 5, wherein $R^3$ is a phenyl group substituted with a carboxyl group and a substituents selected from the group consisting of: an amino group, a halogen atom and a nitro group.

9. The method of claim 5, wherein $R^3$ is a thienyl group substituted with a group represented by the formula (2):

wherein R³⁷ is a 2-pyridyl group, a 3-pyridyl group, or a 4-pyridyl group.

10. A method for expanding CD34⁺ cells, the method comprising:

contacting CD34⁺ cells, in an ex vivo culture, with a stem cell factor (SCF) and at least one compound represented by the formulae below, a tautomer or pharmaceutically acceptable salt of the compound or a solvate thereof:

No. 8
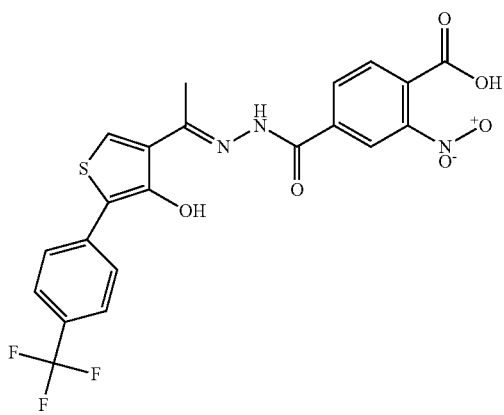
No. 9
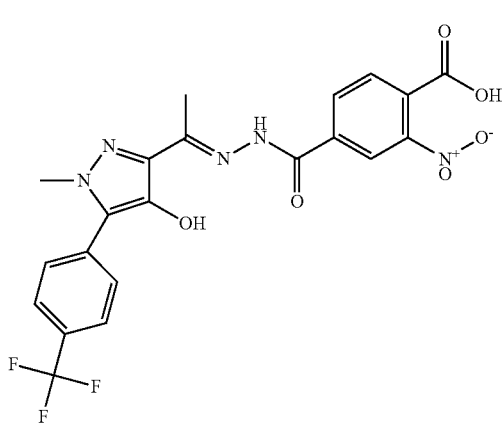
No. 10
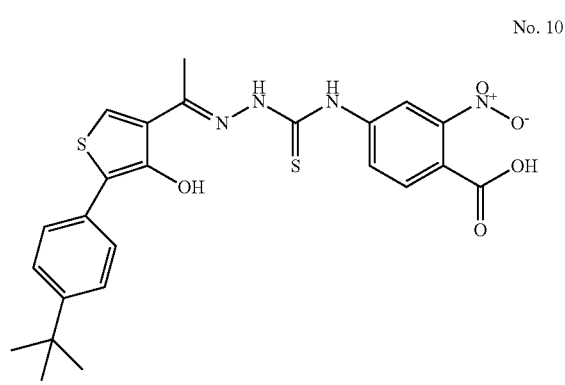
No. 11
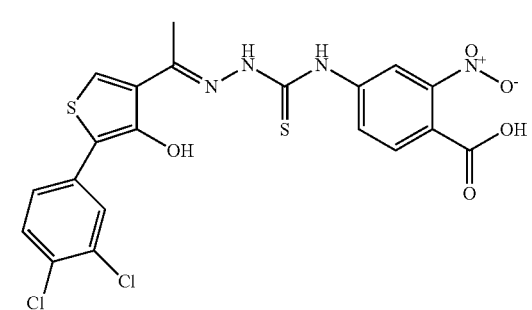
No. 12
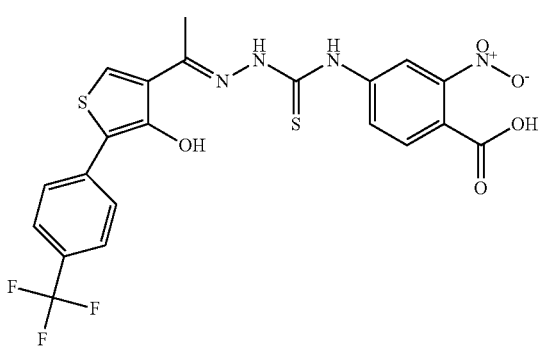
No. 13
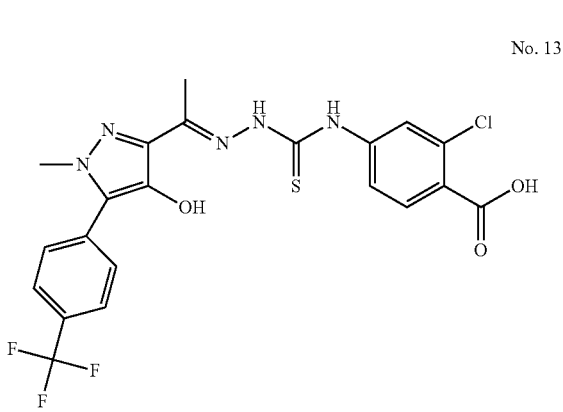
No. 14
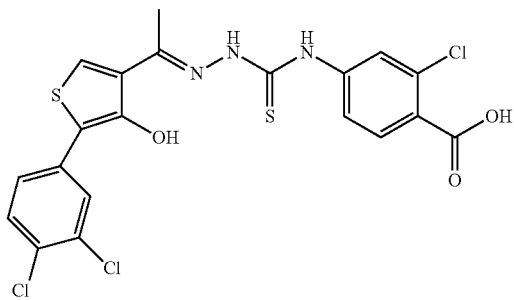
No. 15
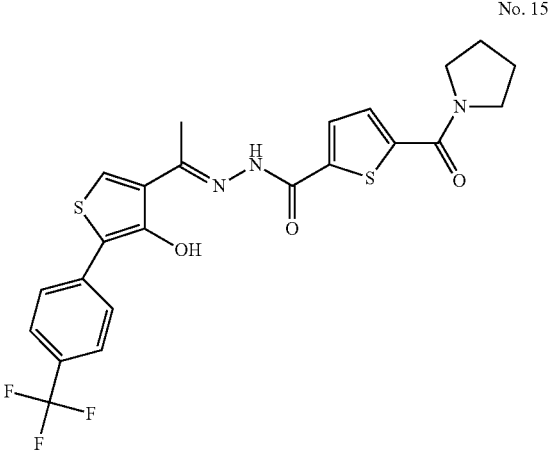

No. 16
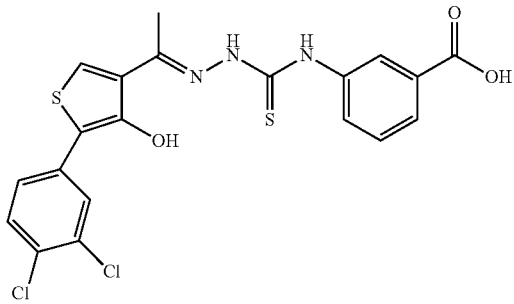
No. 20
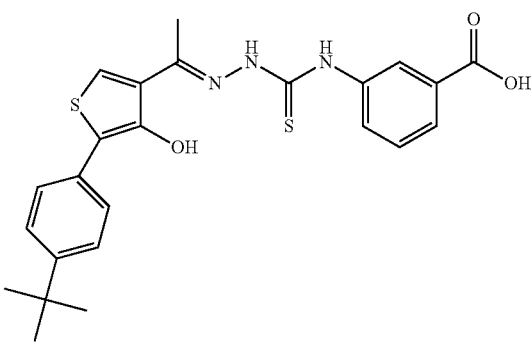
No. 17
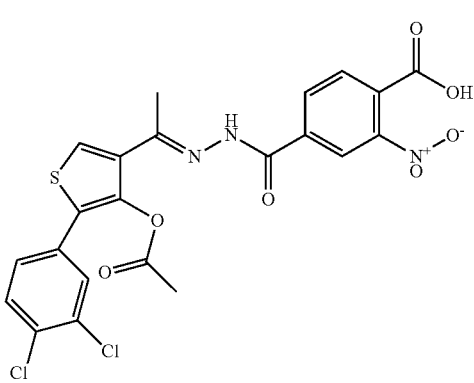
No. 21
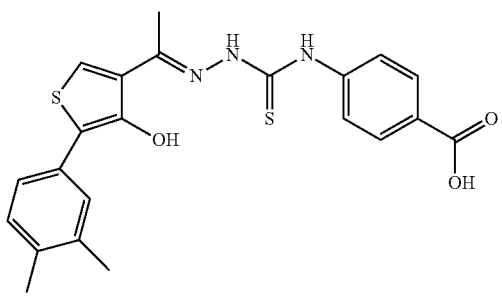
No. 18
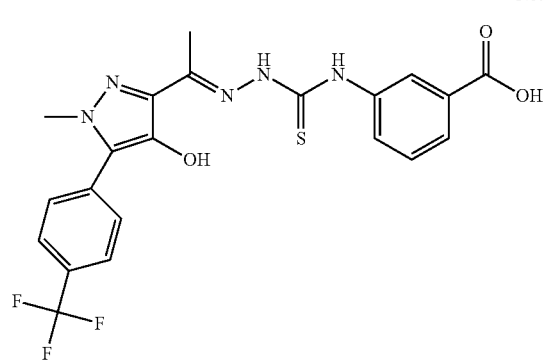
No. 22
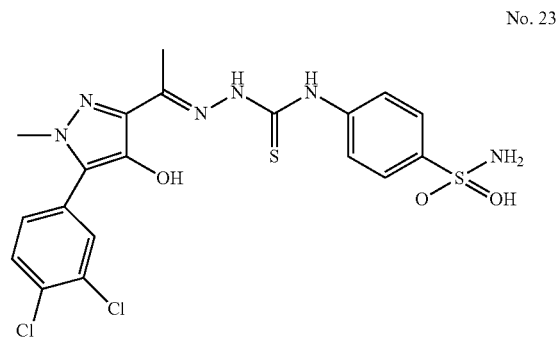
No. 19
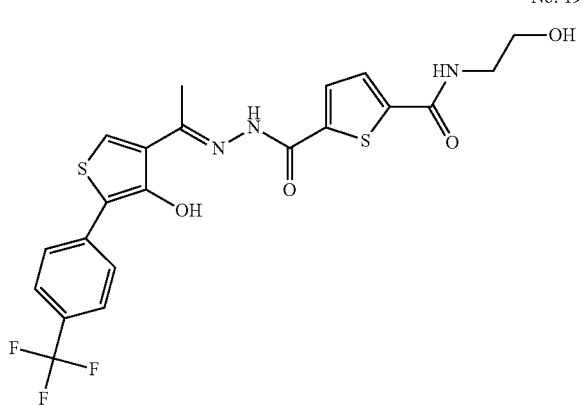
No. 23

No. 24
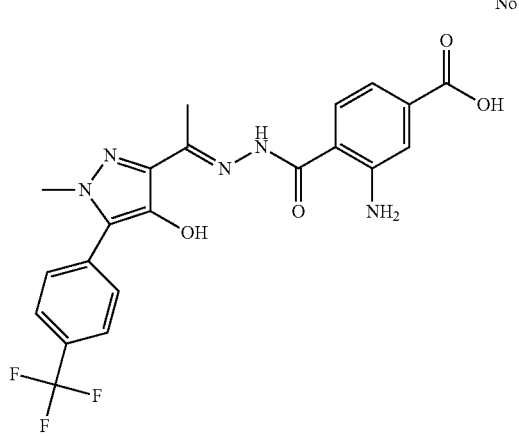
No. 28
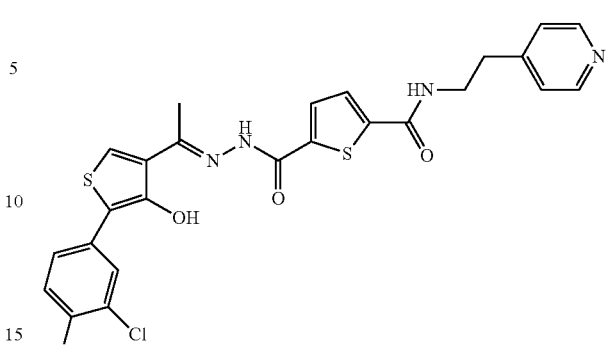
No. 25
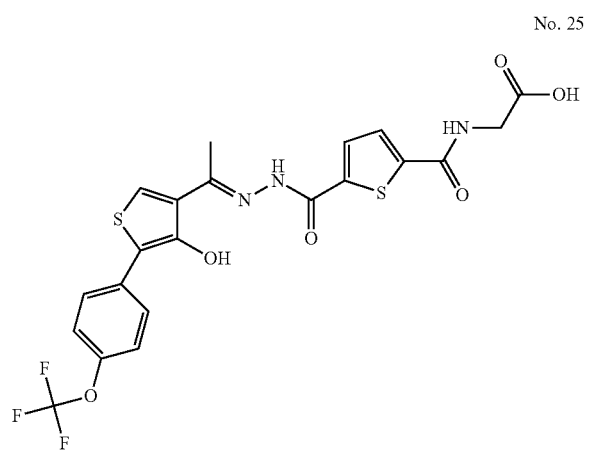
No. 29
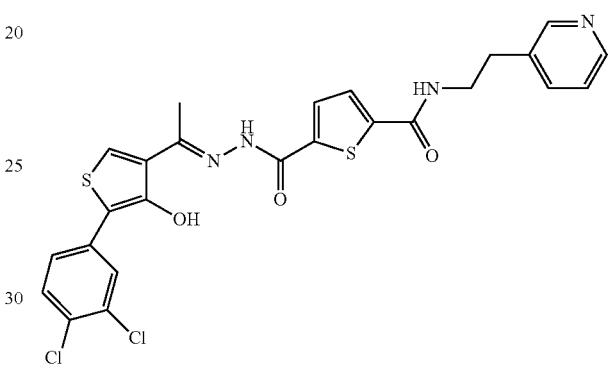
No. 26
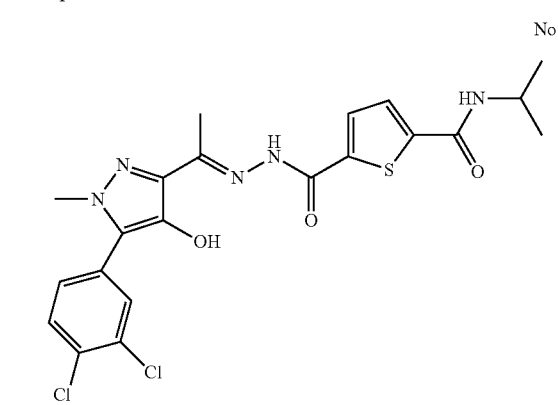
No. 30
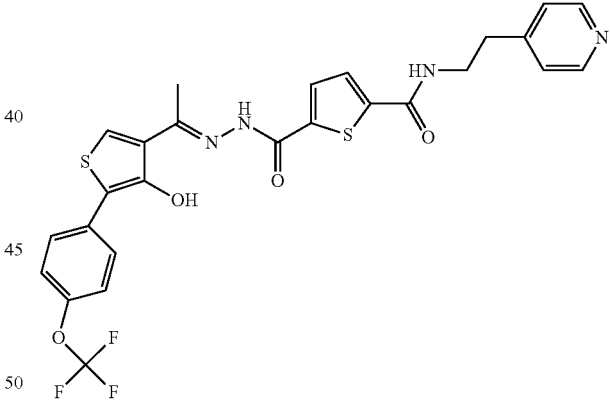
No. 27
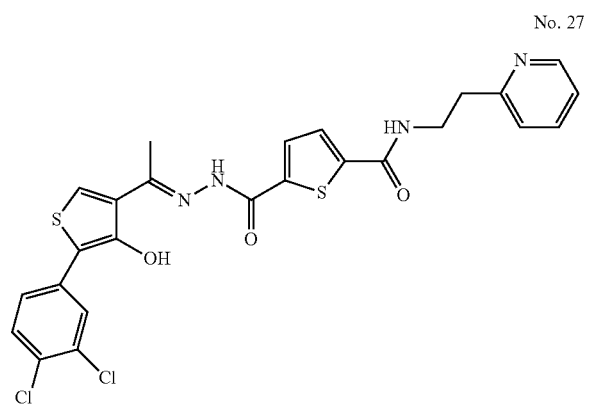
No. 31
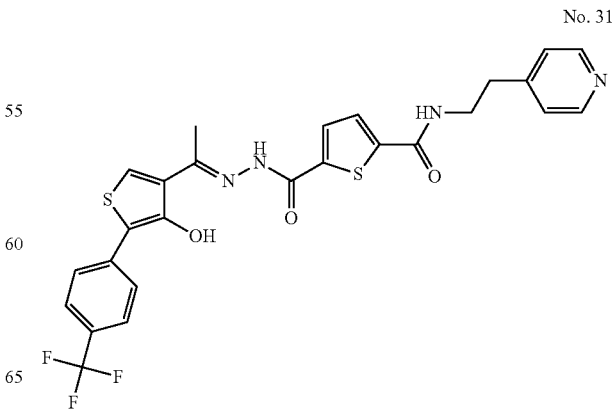

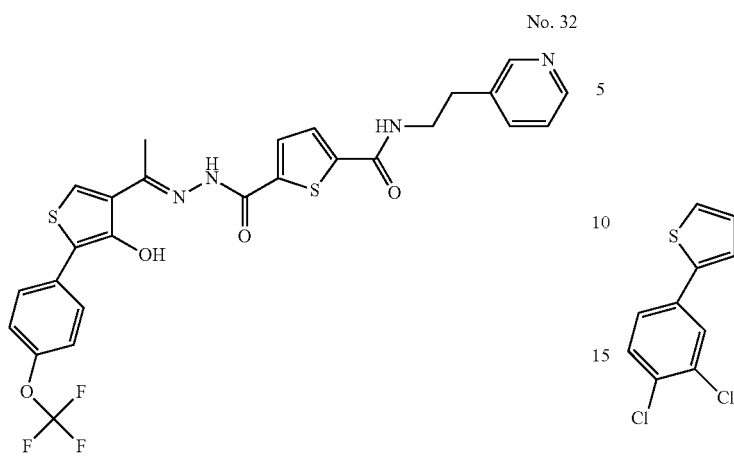
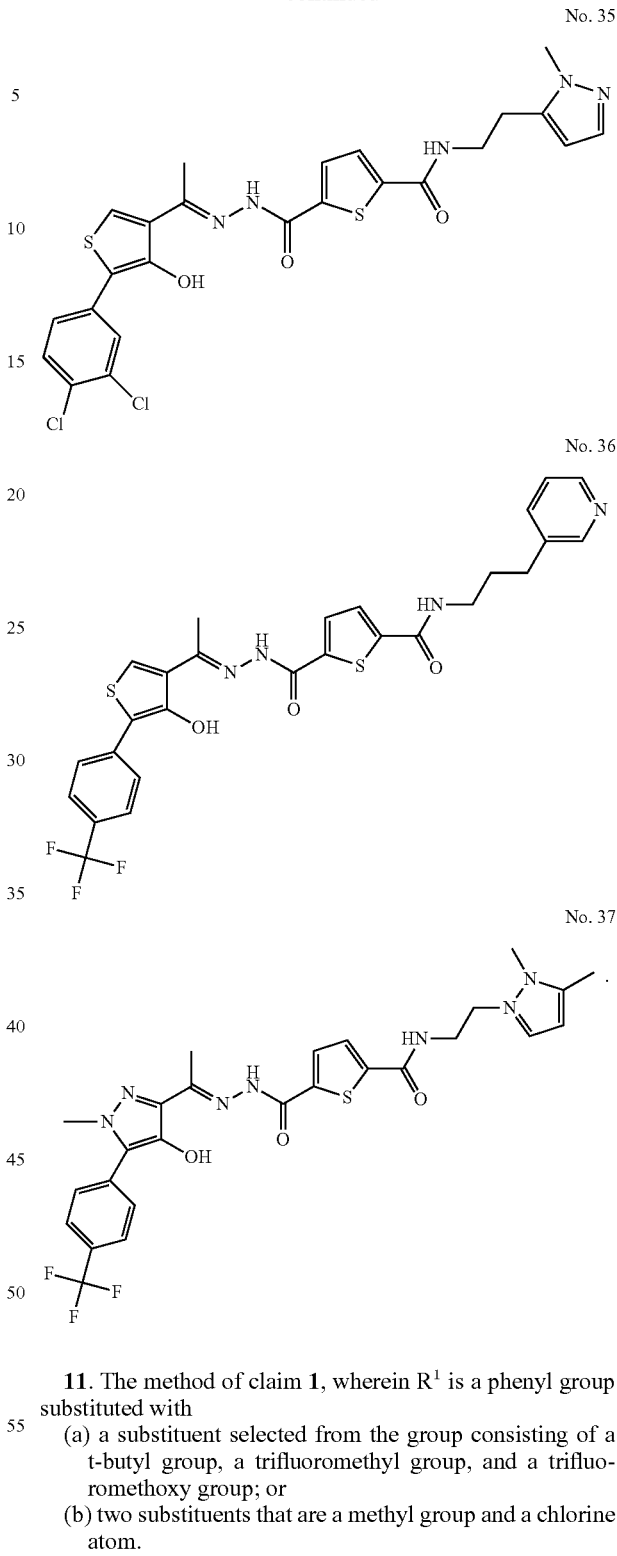
11. The method of claim 1, wherein R[1] is a phenyl group substituted with
(a) a substituent selected from the group consisting of a t-butyl group, a trifluoromethyl group, and a trifluoromethoxy group; or
(b) two substituents that are a methyl group and a chlorine atom.
* * * * *